United States Patent

Johnston

(10) Patent No.: US 9,449,746 B2
(45) Date of Patent: Sep. 20, 2016

(54) METHODS OF MANUFACTURING PLANAR TRANSFORMERS

(71) Applicant: COVIDIEN LP, Mansfield, MA (US)

(72) Inventor: Mark A. Johnston, Boulder, CO (US)

(73) Assignee: Covidien LP, Mansfield, MA (US)

(*) Notice: Subject to any disclaimer, the term of this patent is extended or adjusted under 35 U.S.C. 154(b) by 113 days.

(21) Appl. No.: 14/037,972

(22) Filed: Sep. 26, 2013

(65) Prior Publication Data

US 2014/0104028 A1    Apr. 17, 2014

Related U.S. Application Data

(60) Provisional application No. 61/715,074, filed on Oct. 17, 2012.

(51) Int. Cl.
*H01F 7/06* (2006.01)
*H01F 5/00* (2006.01)
*H01F 41/04* (2006.01)
(Continued)

(52) U.S. Cl.
CPC .......... *H01F 5/003* (2013.01); *H01F 27/2804* (2013.01); *H01F 27/2885* (2013.01); *H01F 27/29* (2013.01); *H01F 41/041* (2013.01); *H01F 2027/2819* (2013.01); *Y10T 29/4902* (2015.01)

(58) Field of Classification Search
CPC .. H01F 5/04; H01F 2005/043; H01F 27/004; H01F 7/0006; H01F 27/2804; H01F 27/2866; H01F 2027/2819; H01F 41/041; Y10T 29/4902; Y10T 29/49071; Y10T 29/49073; Y10T 29/49117; Y10T 29/4913
USPC .............. 29/592.1, 602.1, 604–606, 825; 336/170, 200, 232, 234
See application file for complete search history.

(56) References Cited

U.S. PATENT DOCUMENTS

| | | |
|---|---|---|
| 5,003,622 A | 3/1991 | Ma et al. |
| 5,010,314 A | 4/1991 | Estrov |

(Continued)

FOREIGN PATENT DOCUMENTS

| | | |
|---|---|---|
| CN | 1462456 A | 12/2003 |
| CN | 102237189 A | 11/2011 |

(Continued)

OTHER PUBLICATIONS

Search Report issued on Jan. 17, 2014 in corresponding International patent application No. PCT/US2013/062019.

(Continued)

*Primary Examiner* — Paul D Kim

(57) ABSTRACT

Planar transformers, and corresponding methods of manufacturing planar transformers are disclosed. The planar transformers include circuit layers that reduce termination losses on at least one of the circuit layers. The circuit layers are stacked together in a first direction and include at least first and second circuit layers. The first and second circuit layers each include an electrically conductive trace forming at least one winding having a first termination portion and a second termination portion that are separated by a gap. The gaps of the first and second circuit layers are offset relative to each other in a second direction different from the first direction. The circuit layers may further include a third circuit layer, which includes an electrically conductive trace having a grounded portion that is disposed adjacent to at least one of the gaps of the first and second circuit layers.

6 Claims, 22 Drawing Sheets

(51) Int. Cl.
H01F 27/28 (2006.01)
H01F 27/29 (2006.01)

(56) References Cited

U.S. PATENT DOCUMENTS

| | | | |
|---|---|---|---|
| 5,781,077 A * | 7/1998 | Leitch et al. | 332/117 |
| 5,781,093 A | 7/1998 | Grandmont et al. | |
| 5,847,947 A | 12/1998 | Pan et al. | |
| 5,949,321 A | 9/1999 | Grandmont et al. | |
| 6,211,767 B1 | 4/2001 | Jitaru | |
| 6,307,457 B1 | 10/2001 | Wissink et al. | |
| 6,628,531 B2 * | 9/2003 | Dadafshar | 361/836 |
| 7,248,138 B2 * | 7/2007 | Chiang et al. | 336/200 |
| 7,292,126 B2 | 11/2007 | So | |
| 7,332,993 B1 * | 2/2008 | Nussbaum | 336/200 |
| 7,495,525 B2 | 2/2009 | Ilkov et al. | |
| 8,013,708 B2 | 9/2011 | Tsai | |
| 8,049,301 B2 | 11/2011 | Hui | |
| 8,258,910 B2 | 9/2012 | Herhold | |
| 8,378,775 B2 | 2/2013 | Schiene et al. | |
| 2004/0257190 A1 | 12/2004 | Peck et al. | |
| 2008/0231403 A1 | 9/2008 | Hsu | |
| 2011/0227688 A1 | 9/2011 | Park et al. | |

FOREIGN PATENT DOCUMENTS

| | | |
|---|---|---|
| EP | 0820072 B1 | 1/1999 |
| EP | 1221753 A2 | 7/2002 |
| EP | 1536436 A1 | 6/2005 |
| EP | 1758200 B1 | 4/2008 |
| EP | 2284847 A1 | 2/2011 |

OTHER PUBLICATIONS

China E-Store website, <http://www.p-wholesale.com/cn-pro/5/293to3/planar-telecom-transformer>, product description, Planar Telecom Transformer, printed Dec. 20, 2013. (3 pgs.).
Rhombus Industries, Inc. product brochure, ISDNS-Interface Transformers, printed Sep. 1997. (2 pgs).
Partial Supplementary European Search Report for EP 13 84 6563 dated May 17, 2016.
Notification of the First Office Action for Chinese Appin. No. CN 201380035201.9 dated May 11, 2016.

* cited by examiner

METHODS OF MANUFACTURING PLANAR TRANSFORMERS

CROSS REFERENCE TO RELATED APPLICATION

The present application claims the benefit of and priority to U.S. Provisional Application Ser. No. 61/715,074, filed on Oct. 17, 2012, the entire contents of which are incorporated herein by reference.

BACKGROUND

1. Technical Field

The present disclosure relates to planar transformers. More particularly, the present disclosure relates to planar transformers configured to reduce termination losses.

2. Description of Related Art

Transformers are used in many applications to transfer electrical energy from one circuit to another through inductively coupled conductors or windings. Typical transformers used in electronic devices include a ferromagnetic core around which copper wire is wound to form the primary and secondary windings. In some applications, however, such as in portable electronic devices, typical transformers are too large and heavy. Therefore, many of these electronic devices incorporate planar transformers, which are compact and light weight.

Planar transformers typically include a plurality of stacked circuit layers or PCBs, each of which has an electrically conductive trace that forms one or more transformer windings. The one or more transformer windings on each PCB include a first termination portion through which current enters and a second termination portion through which current exits. When the first and second termination portions are disposed close to one another and are separated by a narrow gap, they may be susceptible to the proximity effect. The proximity effect causes currents flowing through the closely-spaced first and second termination portions to crowd together and flow only in the narrow portions of the first and second termination portions that are closest to the gap. This narrow portion may extend approximately one "skin-depth" from the edges of the first and second termination portions that are disposed adjacent to the gap. As a result, the planar transformer experiences significant power losses commonly referred to as termination losses.

When a power supply providing power to the planar transformer switches at a high frequency, e.g., in the order of 100s of kHz, the "skin depth" of the first and second termination portions may be only a few thousandths of an inch. The resulting termination loss is often the primary cause of conduction loss in planar transformers, often accounting for about 75% of total alternating current (AC) resistance.

SUMMARY

The present disclosure features a planar transformer configured to reduce termination losses to increase power efficiency. In one aspect, the present disclosure features a method for manufacturing a planar transformer. The method includes forming a first electrically conductive trace of at least one winding on a first circuit layer. The first electrically conductive trace includes a first termination portion and a second termination portion defining a first gap therebetween. The method further includes forming a second electrically conductive trace of at least one winding on a second circuit layer. The second electrically conductive trace is formed to include a first termination portion and a second termination portion defining a second gap therebetween so that, when the first and second circuit layers are stacked together in a first direction, the second gap is offset from the first gap in a second direction perpendicular to the first direction.

The method of manufacturing may further include forming a third electrically conductive trace of a grounded portion on a third circuit layer so that the grounded portion aligns with at least one of the first and second gaps in the second direction when the third circuit layer is stacked together with the first and second circuit layers.

The method may further include stacking together the first through third circuit layers so that the third circuit layer is disposed between the first and second circuit layers.

The method for manufacturing may further include stacking together the first and second circuit layers.

The method for manufacturing may further include inserting a core through at least one aperture formed in the first and second circuit layers.

The method for manufacturing may further include assembling the planar transformer with at least one other component for assembling a generator.

The method for manufacturing may further include assembling the planar transformer with at least one other component for assembling a generator of an electrosurgical instrument.

In yet another aspect, the present disclosure features an electrosurgical generator for generating electrosurgical energy. The electrosurgical generator includes a planar transformer. The planar transformer includes a plurality of circuit layers stacked together in a first direction. The plurality of circuit layers includes at least one terminal for outputting electrosurgical energy. The plurality of circuit layers further includes at least a first circuit layer and a second circuit layer, where the first and second circuit layers each include an electrically conductive trace forming at least one transformer winding having a first termination portion and a second termination portion. The first termination portion and the second termination portion define a gap therebetween. The plurality of stacked circuit layers includes means for spreading current flowing through at least one of the first and second termination portions of the first and second circuit layers.

The means for spreading may include disposing the first gap so that it is not disposed adjacent to the second gap.

In another aspect, the present disclosure features a planar transformer having a turn of a winding disposed on two circuit layers. The planar transformer includes a first circuit layer and a second circuit layer stacked together in a first direction. The planar transformer also includes a first electrically conductive trace disposed on the first circuit layer. The first electrically conductive trace forms a first portion of a turn of a winding and has a first termination portion. The planar transformer further includes a second electrically conductive trace disposed on the second circuit layer and electrically coupled to the first electrically conductive trace. The second electrically conductive trace forms the remaining portion of the turn of the winding and has a second termination portion. The first termination portion and the second termination portion are disposed adjacent to each other.

The first and second termination portions may be aligned with each other in the first direction. Also, the winding may be a primary winding of the planar transformer.

The planar transformer may further include a third electrically conductive trace disposed on a third circuit layer and a fourth electrically conductive trace disposed on the fourth circuit layer. The third electrically conductive trace may form at least one winding having a first termination portion and a second termination portion that are separated by a first gap. The fourth electrically conductive trace may form at least one winding having a first termination portion and a second termination portion that are separated by a second gap. The first and second gaps may be offset relative to each other in a second direction different from the first direction.

The at least one winding of the third and fourth circuit layers may be primary windings or secondary windings. Also, the second direction may be perpendicular to the first direction.

The plurality of circuit layers may further include a fifth circuit layer having an electrically conductive trace that forms a grounded portion coupled to ground. The third circuit layer may be disposed so that the grounded portion is laterally aligned with at least one of the gaps in the second direction.

In still another aspect, the present disclosure features a method of manufacturing a planar transformer having a turn of a winding disposed on two circuit layers is also provided in accordance with aspects of the present disclosure. The method of manufacturing the planar transformer comprises forming a first electrically conductive trace into a first portion of a turn of a winding on a first circuit layer. The first electrically conductive trace has a first termination portion at a first end of the portion of the turn. The method further includes forming a second electrically conductive trace into a remaining portion of the turn of the transformer winding on a second circuit layer. The second electrically conductive trace has a second termination portion at a first end of the remaining portion of the turn. The second termination portion is formed so that it is disposed adjacent to the first termination portion when the first and second circuit layers are stacked together. The method further includes forming an electrical via between a second end of the portion of the turn and a second end of the remaining portion of the turn.

The method of manufacturing may further include forming a third electrically conductive trace into at least one transformer winding on a third circuit layer. The third electrically conductive trace may have a first termination portion and a second termination portion that are separated by a first gap. The method of manufacturing may further include forming a fourth electrically conductive trace into at least one other transformer winding on a fourth circuit layer. The fourth electrically conductive trace may have a first termination portion and a second termination portion that are separated by a second gap. The second gap may be laterally offset relative to the first gap when the third and fourth circuit layers are stacked together with the first and second circuit layers.

The method of manufacturing may further include forming a fifth electrically conductive trace into a grounded portion on a fifth circuit layer. The grounded portion may be formed to laterally align with at least one of the first and second gaps when the fifth circuit layer is stacked together with the first through fourth circuit layers.

BRIEF DESCRIPTION OF THE DRAWINGS

Various embodiments of the present disclosure are described herein with reference to the drawings, wherein.

DETAILED DESCRIPTION

Figure 1:
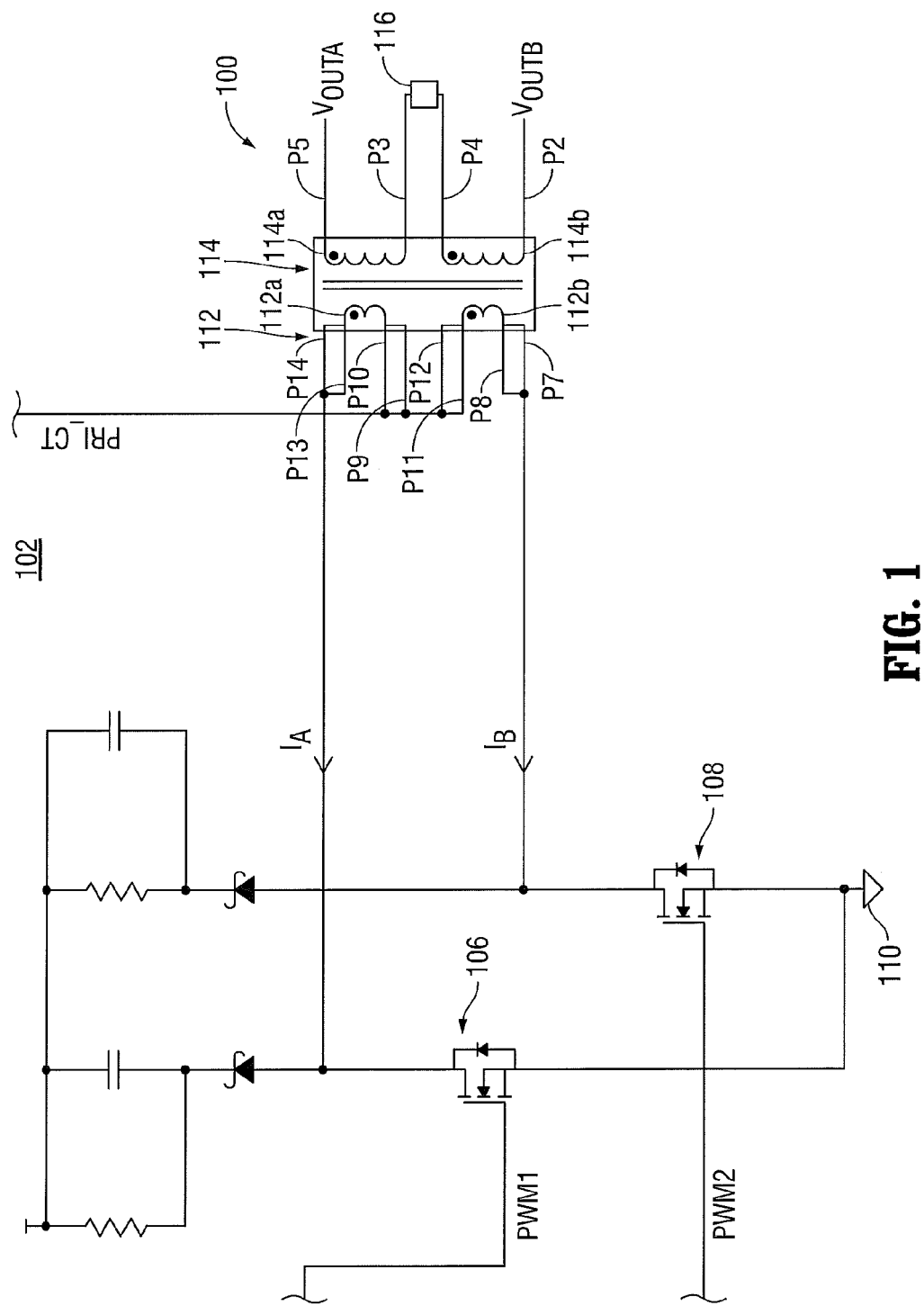
FIG. 1 is a schematic circuit diagram of an exemplary power stage of a generator that may incorporate a planar transformer in accordance with embodiments of the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

The present disclosure is directed to a planar transformer that includes a plurality of circuit layers that are stacked in a first direction. Each circuit layer may be a printed circuit board (PCB) that includes an electrically conductive trace forming a transformer winding. The trace includes a first termination portion through which current enters the winding and a second termination portion through which current exits the winding. The first termination portion and the second termination portion are separated by a gap. The transformer winding is a primary or secondary winding and may include a single turn or a plurality of turns.

In the configuration described above, current flows in opposite directions on both sides of the gap, which creates a condition in which the proximity effect may cause current to flow in only a narrow portion of the first and second termination portions. In some cases, this narrow portion may extend approximately one skin depth away from the gap. When the current crowds together in the narrow portions of the first and second termination portions, there may be significant power loss.

The planar transformers according to the present disclosure are configured to spread the current so that it flows more uniformly through a larger portion of the first and second termination portions. In some embodiments, the circuit layers are arranged so that the gaps between the first and second termination portions in at least first and second circuit layers in the stack are laterally offset from one another in a second direction that is perpendicular to the first direction. In other embodiments, a circuit layer includes a grounded portion that is positioned adjacent to the gap between the first and second termination portions of another circuit layer. In yet other embodiments, the stack of circuit layers includes circuit layers that incorporate a combination of the configurations described above, e.g., at least two circuit layers where the gaps of these circuit layers are offset laterally from each other and at least one other circuit layer has a grounded portion positioned adjacent to the gaps.

FIG. 1 shows an exemplary RF inverter circuit 102 that may incorporate a planar transformer 100 according to embodiments of the present disclosure. The planar transformer 100 is coupled to first and second push-pull switches 106, 108. The planar transformer 100 converts a direct current (DC) provided by a power supply, e.g., a battery, into an alternating current (AC).

The planar transformer 100 is configured to include split primary windings 112 having first and second primary windings 112a and 112b, respectively, and split secondary windings 114 having first and second secondary windings 114a and 114b, respectively. In the embodiment shown in FIG. 1, the planar transformer 100 is configured as a 1:1:4:4 transformer, in which the first and second primary windings 112a and 112b each include one turn, and the first and second secondary windings 114a and 114b each include four turns. It is envisioned that other transformer configurations may be employed, such as 2:2:4:4 and 2:2:8:8.

A microcontroller (e.g., the microcontroller 104 of FIG. 19) outputs control signals PWM1 and PWM2 to control switches 106 and 108, respectively, so that switches 106 and 108 alternately allow current to flow through them. In embodiments, the microcontroller controls the switches 106 and 108 so that the AC output signal oscillates at a predetermined frequency, e.g., 472 kHz.

The switches 106 and 108 may be transistors, e.g., N-type, P-type, or MOSFET transistors. Other types of transistors and switches may also be employed. The signals PWM1 and PWM2 are provided to respective gates of switches 106, 108, for controlling switches 106 and 108 to alternately conduct current. The signals PWM1 and PWM2 may be square waves that are 180° out of phase with respect to each other In embodiments of the present disclosure, the transformer 100 is a planar transformer implemented on a substrate, such as the substrate of a circuit layer. In such an implementation, the planar transformer may include a plurality of pins P2-P5 and P7-P14.

During operation in a first phase, when the switch 106 is closed in response to the PWM1 signal, current $I_A$ flows from the power source line PRI_CT to ground 110 via the first primary winding 112a (i.e., via pins P9, P10, P13, P14) and the switch 106. The current flowing through the first primary winding 112a induces a current in the first secondary winding 114a and the second secondary winding 114b. The induced current flows from pin P2 to pins P4 and P3, which are effectively connected in series through series capacitors 116, via the second secondary winding 114b. The induced current then flows from pin P3 to pin P5 via the first secondary winding 114a. The induced current then flows to a load connected across pins P2 and P5. This results in a voltage $V_{OUTA}$ at pin P5.

In a second phase, when the switch 108 is closed in response to the PWM2 signal, current $I_B$ flows from the power source line PRI_CT to ground 110 via the second primary winding 112b (i.e., via pins P11, P12, P7, P8) and the switch 108. The current flowing through the second primary winding 112b induces a current in the first secondary winding 114a and the second secondary winding 114b. The induced current flows from pin P5 to pins P3 and P4 via the first secondary winding 114a. The induced current then flows from pin P4 to pin P2 via the second secondary winding 114b. The induced current then flows to a load connected across pins P2 and P5. This results in a voltage $V_{OUTB}$ at pin P2.

In some embodiments described in more detail below, voltages $V_{OUTA}$ and $V_{OUTB}$ are provided to opposing jaw members of an electrosurgical instrument. The voltages $V_{OUTA}$ and $V_{OUTB}$ may have a pseudo-square waveform with a predetermined output range, such as 150 W, 85 Vrms, and 3 Arms.

Figure 2:
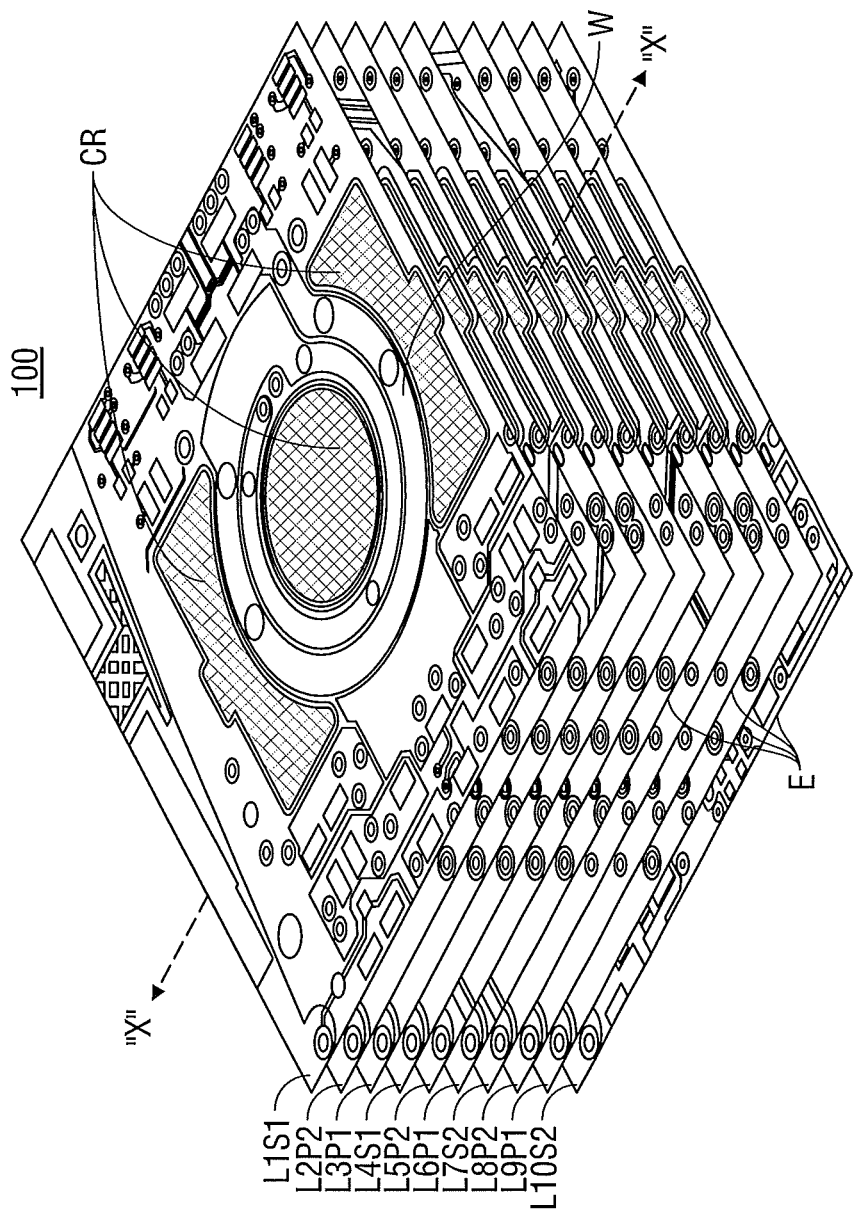
FIG. 2 is an exploded perspective view of a planar transformer in accordance with an embodiment of the present disclosure that may be used in the exemplary power stage of FIG. 1.

FIG. 2 is a perspective view of an exemplary embodiment of a planar transformer 100 having ten circuit layers L1S1, L2P2, L3P1, L4S1, L5P2, L6P1, L7S2, L8P2, L9P1, and L10S2, where L1-L10 refer to the particular circuit layer, P1 and P2 refer to the first and second primary windings 112a and 112b, respectively, and S1 and S2 refer to the first and second secondary windings, 114a and 114b, respectively. An edge E associated with each layer L1-L10 is aligned with a corresponding edge E of layers positioned above or below the respective layer.

Each circuit layer L1-L10 may be a PCB that includes traces formed on a substrate. The traces are formed of a conductive material, e.g., copper, and the substrate is formed of a nonconductive material, e.g., polytetrafluoroethylene (Teflon®) or woven glass and epoxy. The traces may be etched or deposited on the substrate.

In embodiments, the circuit layers L1-L10 are stacked. FIG. 2 shows PCBs stacked in a vertical direction, however any direction is envisioned. Once stacked, the stack can be oriented in any direction. The vertical stack is used throughout the disclosure by way of example only and to provide a convenient directional frame of reference.

Each circuit layer may include an aperture. When layers L1-L10 are stacked, the apertures of the respective layers L1-L10 are aligned and a core CR made of a magnetic material, e.g., a ferrite, is inserted through the apertures of the circuit layers L1-L10 and positioned so that the core CR is disposed adjacent to the winding W of each circuit layer L1-L10.

Figure 3:
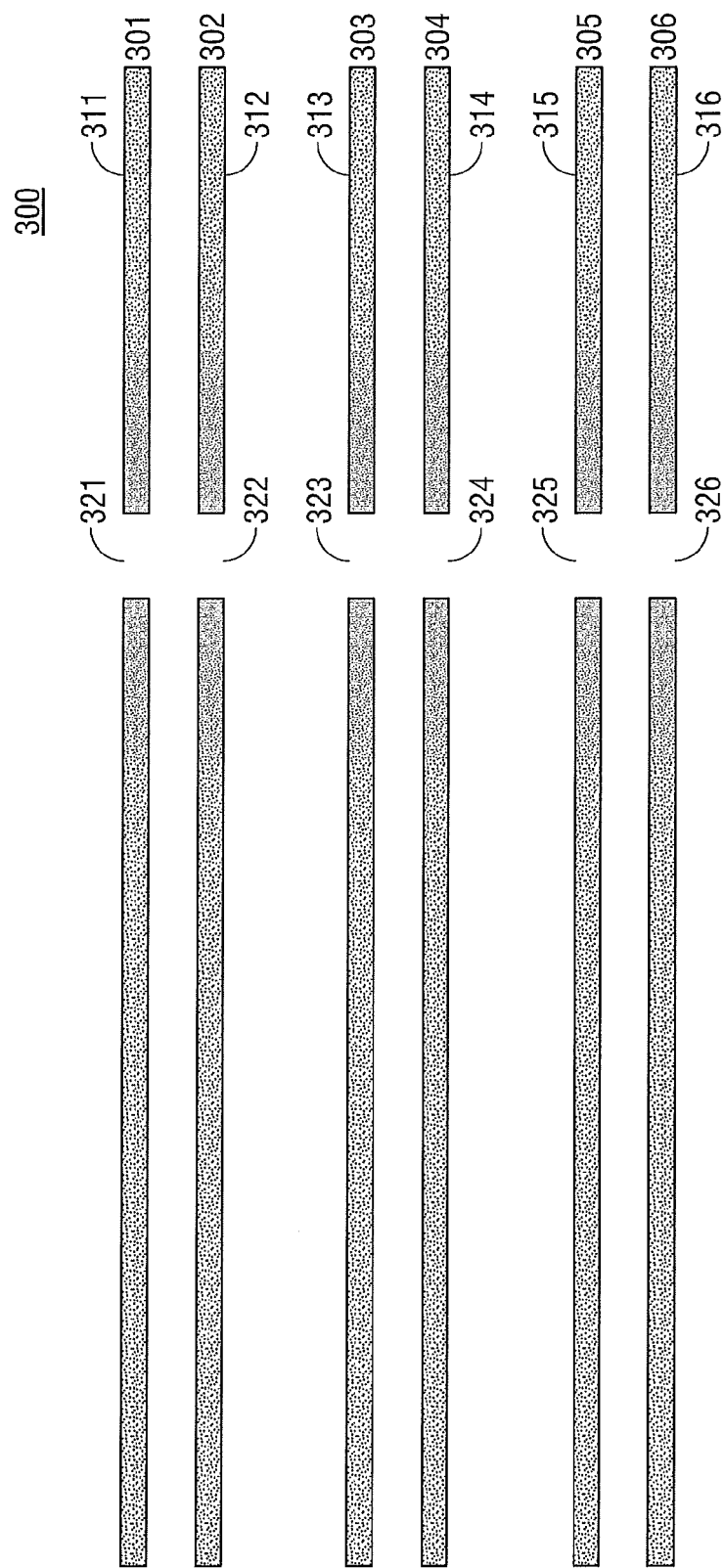
FIG. 3 is a cross-sectional side view of a planar transformer illustrating the proximity effect that is addressed by the planar transformers according to embodiments of the present disclosure.

FIG. 3 shows a cross-sectional view of a transformer 300 that illustrates crowding of current as a result of the proximity effect. The planar transformer 300 includes circuit layers 301-306 having conductive traces 311-316, respectively. The conductive traces 311-316 form windings of the planar transformer 300. The windings include first termination portions and second termination portions that are separated by gaps 321-326. As shown, the gaps 321-326 are vertically aligned with each other. When current enters the first termination portions and exits the second termination portions, the current flows on opposite sides of each gap 321-326 in opposite directions. As described above, in this configuration the current concentrates in narrow portions of the first and second termination portions that are adjacent to the gaps 321-326.

Figure 4:
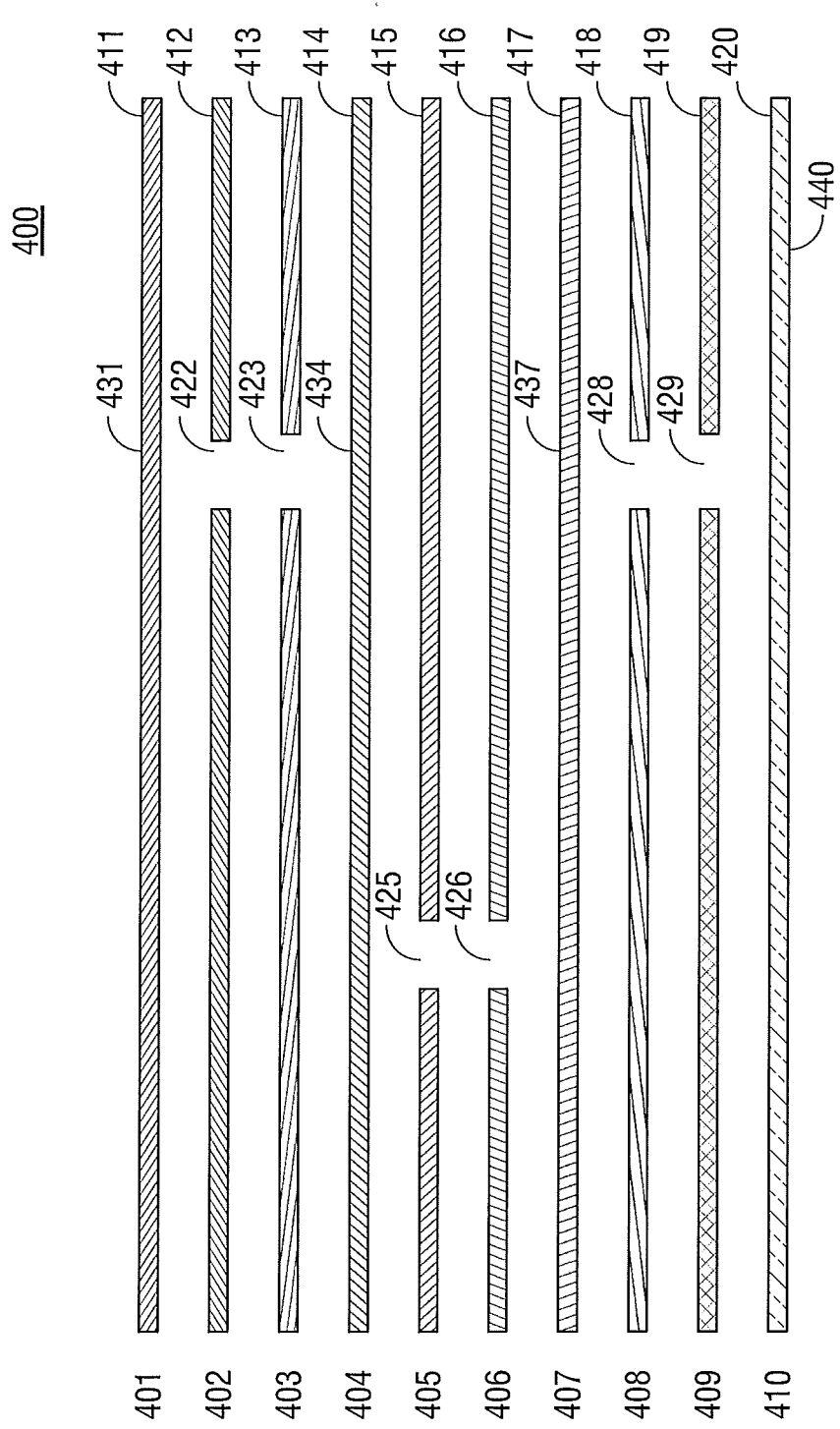
FIG. 4 is a cross-sectional side view of the planar transformer of FIG. 2.

FIGS. 4-7 show a variety of embodiments of planar transformers in which the circuit layers are configured and/or arranged to mitigate the proximity effect. With reference to FIG. 4, an exemplary planar transformer 400 according to one embodiment includes circuit layers 401-410. Each circuit layer 401-410 includes a respective conductive trace 411-420 that forms a winding of the planar transformer 400. Specifically, conductive traces 412, 413, 415, 416, 418, and 419 form the primary windings and conductive traces 411, 414, 417, and 420 form the secondary windings. In the embodiment shown in FIG. 4, only the primary windings of the circuit layers 401-410 include first termination portions and second termination portions that are separated by gaps 422, 423, 425, 426, 428, and 429.

In other embodiments, the secondary windings 411, 414, 417, and 420 may also include first and second termination portions that are separated by narrow gaps, which may cause the current to concentrate in the first and second termination portions near the narrow gaps as a result of the proximity effect. Also, the primary windings 412, 413, 415, 416, 418, and 419 may include one or more turns and the secondary windings 411, 414, 417, and 420 may include one or more turns.

The circuit layers 401-410 of FIG. 4 are configured and arranged to counteract the proximity effect by spreading the current away from the narrow portions of the first and second termination portions that are adjacent to the gaps 422, 423, 425, 426, 428, and 429. First, the circuit layers 401-410 are configured and arranged so that different groups of gaps 422, 423, 425, 426, 428, and 429 are laterally offset relative to each other. In the specific embodiment of FIG. 4, gaps 422 and 423 are laterally offset relative to gaps 425, 426, 428, and 429 in a direction perpendicular to the direction in which the circuit layers 401-410 are stacked. Thus, gaps 423 and 425 are not vertically aligned, and gaps 426 and 428 are not vertically aligned. In this configuration, the current flowing through the first and second termination portions of the windings is spread more uniformly through the first and second termination portions.

Second, circuit layers 401, 404, 407, and 410 having respective grounded portions 431, 434, 437, and 440 are arranged between pairs or groups of circuit layers having gaps 422, 423, 425, 426, 428, and 429 so that the grounded portions 431, 434, 437, and 440 are positioned immediately adjacent to at least one of the gaps 422, 423, 425, 426, 428, and 429. Specifically, grounded portion 431 is located immediately adjacent to gap 422, grounded portion 434 is located between gaps 423 and 425, grounded portion 437 is located between gaps 426 and 428, and grounded portion 440 is located immediately adjacent to gap 429.

The positioning of the grounded portions 431, 434, 437, and 440 immediately adjacent to at least one of the gaps 422, 423, 425, 426, 428, and 429 reduces termination loss at least as follows. The currents flowing through the first and second termination portions of the winding 412 near the gap 422 cause an eddy current to develop in the adjacent grounded portion 431. The eddy current flows in a direction opposite to the direction of the current flowing in the first and second termination portion of the conductive traces 412. The proximity of the eddy current in the grounded portion 431 and the current flowing in the opposite direction in the winding 412 causes the current flowing through first and second termination portions of the winding 412 to spread so that the current flowing through winding 412 flows through a larger portion of winding 412, thus reducing the proximity effect and reducing termination losses in the winding 412. Similarly, eddy currents are established in the grounded portions 434, 437, and 440. These eddy currents represent current losses. However, the current losses caused by these eddy currents are more than offset by the reduction in current losses provided by the grounded portions 431, 434, 437, and 440.

Accordingly, for each layer 401-410 in which current enters a winding at a first termination portion and exits the winding at a second termination portion, the layers 401-410 are configured and/or arranged to counteract the proximity effect such that current flowing through the first and second termination portions will be spread and termination loss reduced.

Some of the gaps 422, 423, 425, 426, 428, and 429 are vertically aligned. For example, gaps 422 and 423 are aligned with one another. However, the proximity effect is mitigated due to the grounded portions 431 and 434 that are provided directly adjacent to and vertically aligned with gaps 422 and 423. Additionally, gaps 422 and 423 are vertically aligned with gaps 428 and 429. The gaps 423 and 428 are not affected by the proximity effect because they are not adjacent to one another, but rather are spaced vertically from one another and are further separated by multiple layers, that is, layers 404-407.

In a simulated experiment, total power loss associated with planar transformers 300 and 400 shown in FIGS. 3 and 4, respectively, were calculated and compared. The total power loss determined for planar transformer 400 was reduced by a factor greater than three relative to the total power loss determined for transformer 300.

Various configurations using any combination of the first and/or second method for mitigating the proximity effect are envisioned. For example, in another embodiment shown in FIG. 5, a planar transformer 500 is shown having eight layers 501-508, each of which is provided with a conductive trace 511-518. Windings are formed in the respective conductive traces 511-518. Gaps 521, 522, 524, 525, 527, and 528 are formed between corresponding first and second termination portions of the associated traces 511, 512, 514, 515, 517, and 518. Since current flows on both sides of gaps 521, 522, 524, 525, 527, and 528, the planar transformer 500 is susceptible to the proximity effect.

Figure 5:
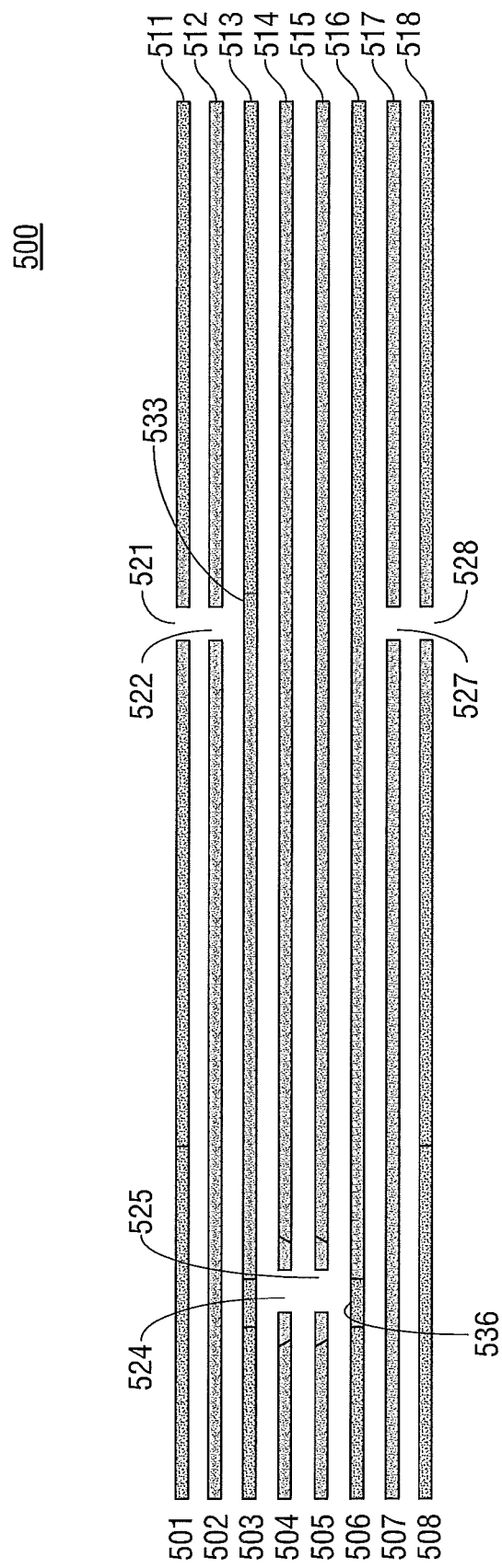
FIG. 5 is a cross-sectional side view of a planar transformer in accordance with yet another embodiment of the present disclosure.

The embodiment of FIG. 5 employs the first and second methods for mitigating the proximity effect. The difference between this configuration and the configuration shown in FIG. 4 is that the top and bottom layers 501 and 508 do not have grounded portions. In this embodiment, the gaps 521 and 528 are vertically aligned with adjacent gaps, 522 and 527, respectively, but are not adjacent to any grounded portion, i.e., grounded portions 533 and 536. The gaps 521, 522, 527, and 528, however, are offset from non-adjacent gaps 524 and 525, which provide reductions in termination losses. The other gaps 522, 524, 525, and 527 are adjacent to one of the grounded portions 503 and 506, thus mitigating any termination loss caused by the vertically-aligned gaps.

Figure 6:
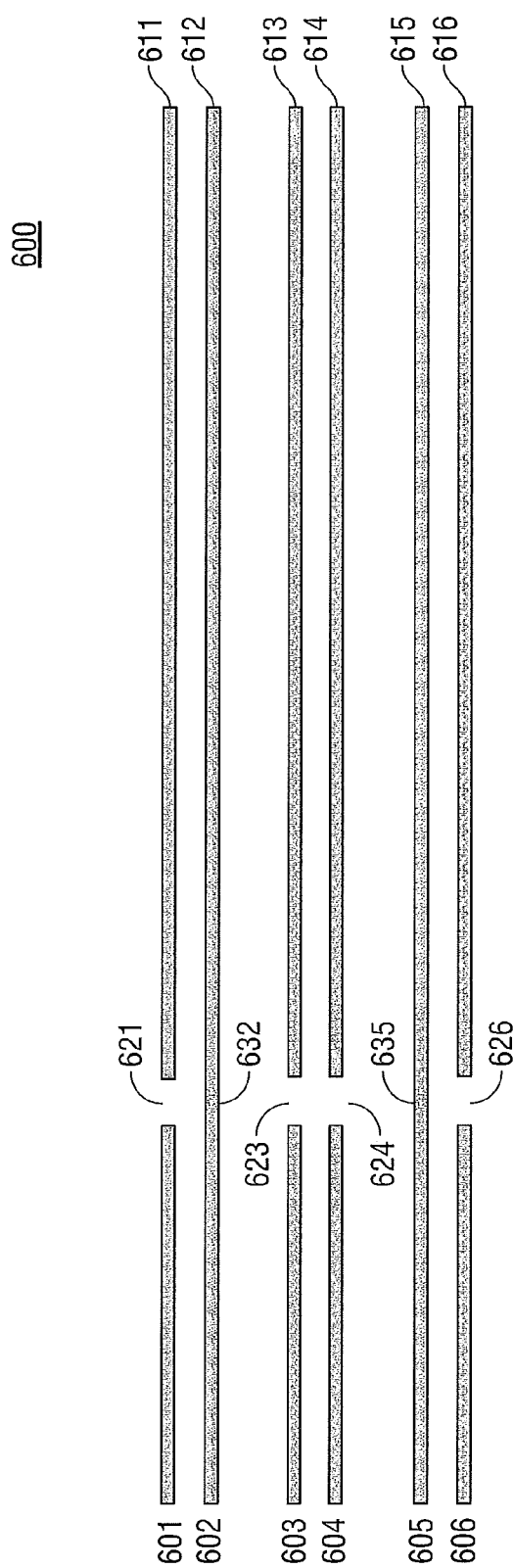
FIG. 6 is a cross-sectional side view of a planar transformer in accordance with still another embodiment of the present disclosure.

FIG. 6 illustrates a planar transformer 600 in accordance with another embodiment of the present disclosure. The planar transformer 600 includes six circuit layers 601-606. Each circuit layer 601-606 includes a respective conductive trace 611-616 that forms a winding of the planar transformer 600. The gaps 621, 623, 624, and 626 are formed between first and second termination portions of the respective conductive traces 611, 613, 614, and 616. Unlike the planar transformers 400 and 500 of FIGS. 4 and 5, respectively, the gaps 621, 623, and 624 are vertically aligned. The conductive traces 612 and 615 include grounded portions 632 and 635, respectively. In this embodiment, each gap 621, 623, 624, and 626 is adjacent to one of the grounded portions 632 and 635, thus mitigating any termination losses caused by the vertically-aligned gaps 621, 623, 624, and 626.

Figure 7:
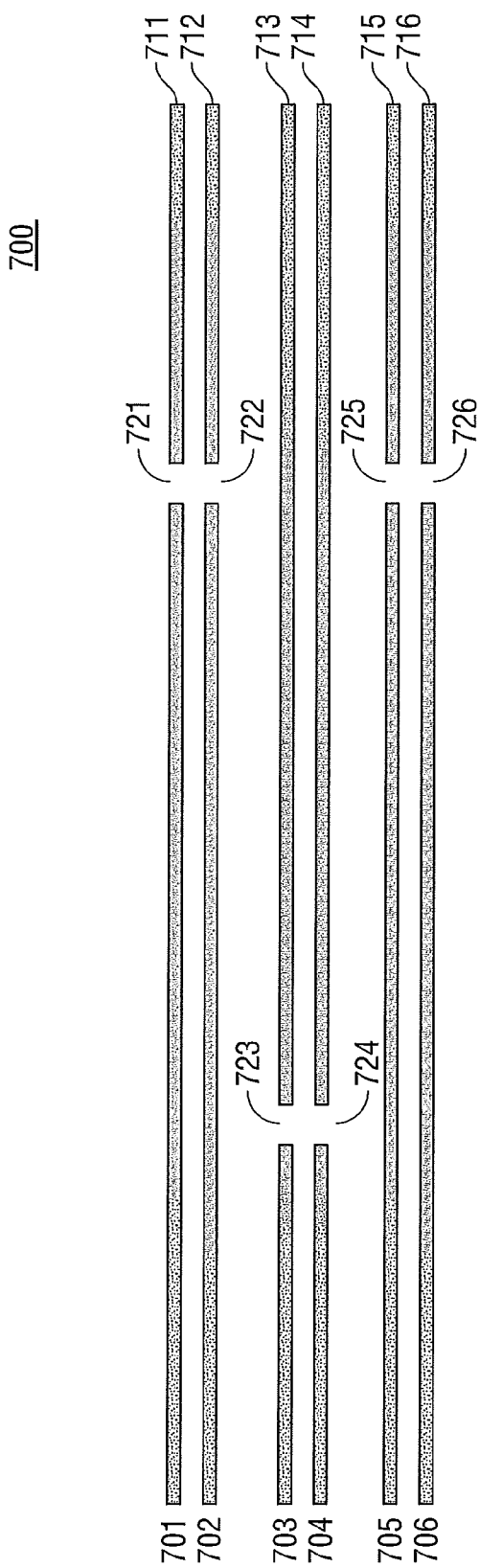
FIG. 7 is a cross-sectional side view of a planar transformer in accordance with still another embodiment of the present disclosure.

FIG. 7 shows a planar transformer 700 in accordance with another embodiment of the present disclosure. The planar transformer 700 includes six circuit layers 701-706. Each circuit layer 701-706 includes a conductive trace 711-716 that forms a winding. Gaps 721-726 are formed between corresponding first and second termination portions of the associated conductive traces 711-716. In this embodiment, the proximity effect is mitigated by laterally offsetting groups of gaps relative to one another. Specifically, gaps 723 and 724 are laterally offset from gaps 721 and 722, and from gaps 725 and 726. Although gaps 722 and 725 are aligned with each other, they are sufficiently offset from one another to reduce or eliminate the proximity effect between themselves.

Simulation software may be used to optimize the parameters of the stack of circuit layers, e.g., the positioning of gaps with respect to each other. The simulation software may include two-dimensional finite element analysis software, which solves electromagnetic field equations to determine the current distribution in cross-sections of a stack of circuit layers.

FIGS. 8-17 show each of the circuit layers of the planar transformer 100 of FIG. 2. The configuration of the circuit layers shown in FIGS. 8-17 corresponds to the configuration of circuit layers shown in the cross-sectional view of FIG. 4. The pins P2-P5 and P7-P14 associated with planar transformer 100 are shown in FIGS. 8-17 with a suffix LN, where N indicates the layer (1-10) shown in the associated figure.

With reference to FIGS. 8, 11, 14, and 17, the layers L1S1, L4S1, L7S2, and L10S2 are associated with the secondary winding 114. The first and fourth layers L1S1 and L4S1 of FIGS. 8 and 11, respectively, are associated with the first secondary winding 114a, which includes four turns W1S1, W2S1, W3S1, and W4S1. The seventh and tenth layers L7S2 and L10S2 of FIGS. 14 and 17, respectively, are associated with the second secondary winding 114b, which includes four turns W1S2, W2S2, W3S2, and W4S2. The turns W1S1 and W1S2 are electrically connected in series. It follows that turns W1S1, W2S1, W3S1, W4S1, W1S2, W2S2, W3S2, and W4S2 are all electrically connected in series.

Figure 8:
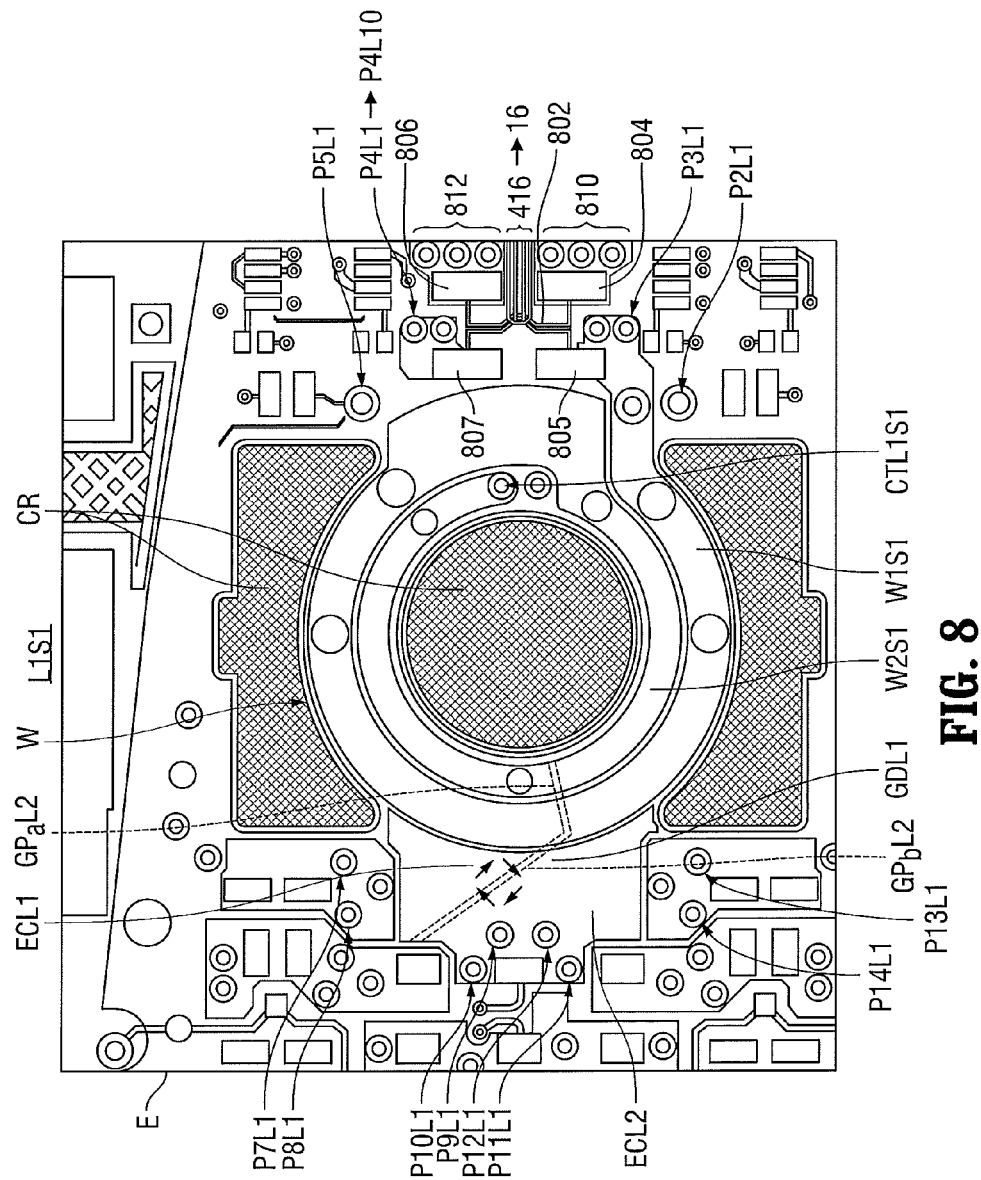
FIG. 8 is a top view of a first layer of the planar transformer of FIG. 2 illustrating a gap between traces disposed on a second layer of the planar transformer of FIG. 2.
Figure 17:
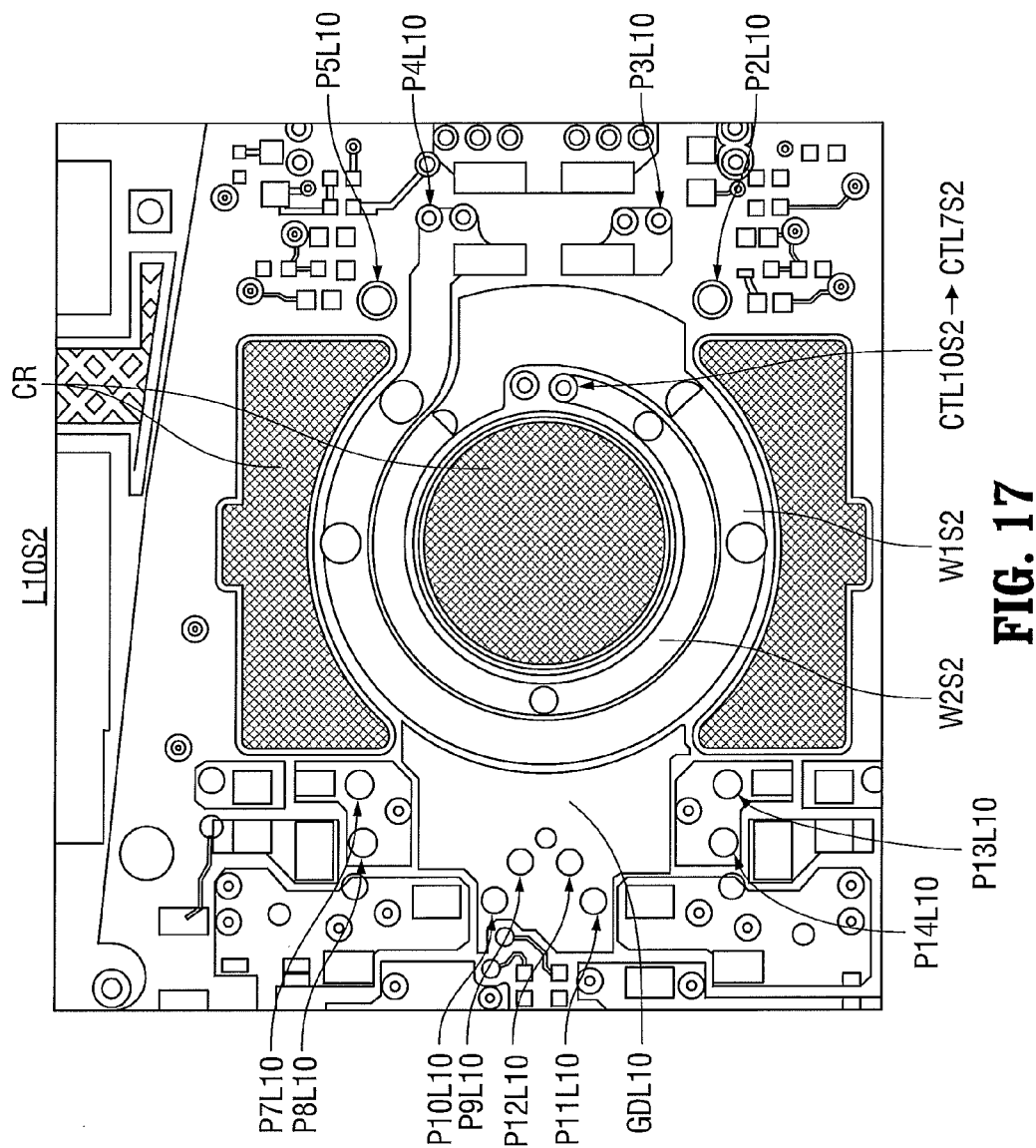
FIG. 17 is a top view of a tenth layer of the planar transformer of FIG. 2.

As shown in FIG. 8, the first turn W1S1 of the first secondary winding 114a is electrically connected in series via pins P3L1 and P4L1 to the first turn W1S2 of the second secondary winding 114b that is located on the tenth layer L10S2 shown in FIG. 17. The first turn W1S1 is electrically connected to pin P3L1, which is electrically coupled to pin P4L1 via a first capacitor that is electrically connected between contacts 804 and 805, a conductive trace 802 that is electrically connected between the contacts 804 and 806, and a second capacitor that is electrically connected between contacts 806 and 807. The contact 804 is electrically connected to three electrical vias 810 and the contact 806 is electrically connected to three other electrical vias 812. Pin P4L1 is electrically connected to pin P4L10 located on layer L10S2 and pin P3L1 is electrically connected to pin P3L10 located on layer L10S2. Electrical pathways (not shown) are provided to make the electrical connections between pins or contacts located on different layers. The electrical pathways may include vias.

Figure 11:
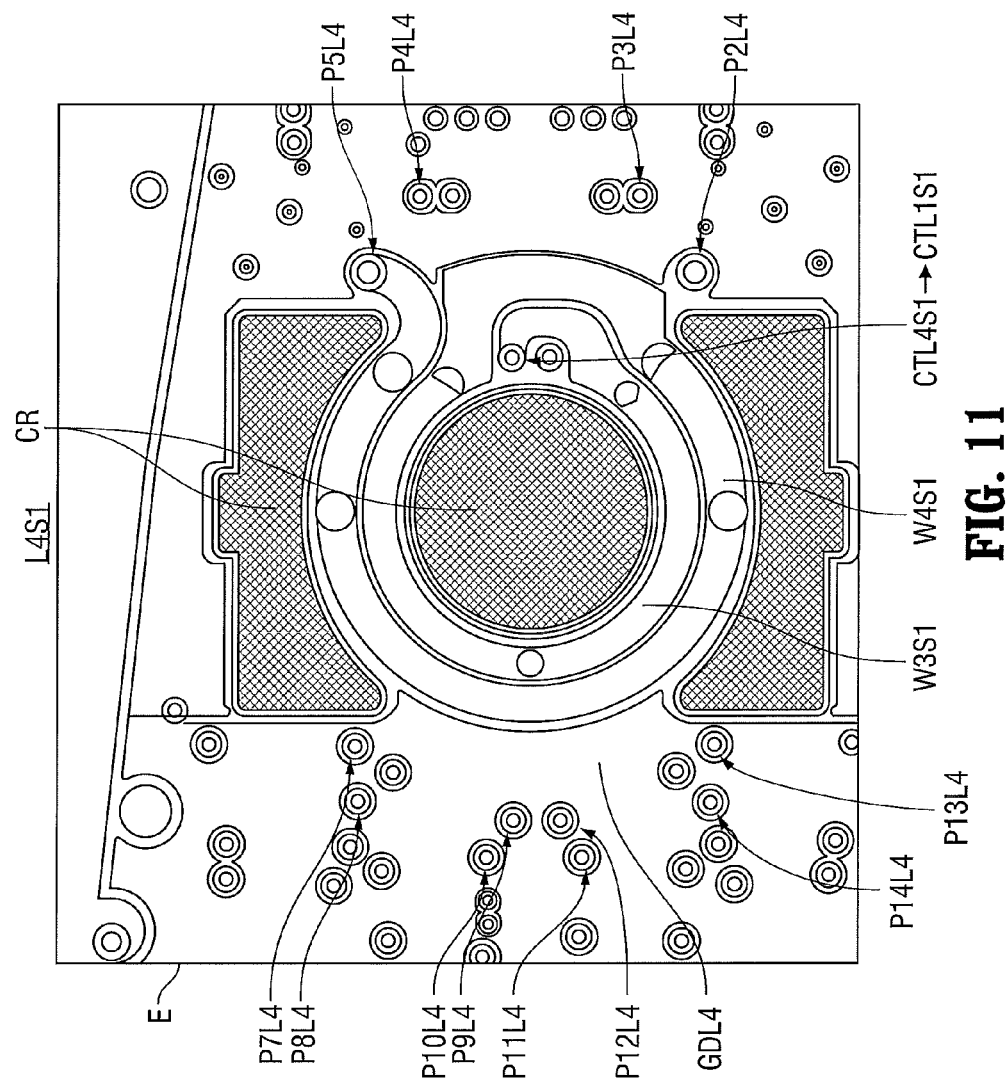
FIG. 11 is a top view of a fourth layer of the planar transformer of FIG. 2.

The first layer L1S1 further includes the second turn W2S1 of the first secondary winding 114a that is electrically connected to the third turn W3S1 of the first secondary winding 114a that is located on the fourth layer L4S1 shown in FIG. 11. The second turn W2S1 is electrically connected to contact CTL1S1 located on the first layer L1S1 that is electrically connected to the contact CTL4S1 located on the fourth layer L4S1.

The fourth layer L4S1, shown in FIG. 11, includes the third turn W3S1 of the first secondary winding 114a. The third turn W3S1 is electrically connected via connector CTL4S1 to the second turn W2S1 located on the first layer L1S1 shown in FIG. 8. The fourth layer L4S1 further includes a fourth turn W4S1 of the first secondary winding 114a that is electrically connected to pin P5L4, which electrically connects to the load. Pin P5L4 is electrically connected to pin P5L6 located on the sixth layer L6P1, which is electrically connected to trace $TV_{OUTA}$. The trace $TV_{OUTA}$ traverses the sixth layer L6P1 to edge E of the sixth layer L6P1 where the trace $TV_{OUTA}$ exits the sixth layer L6P1.

The tenth layer L10S2, shown in FIG. 17, includes the first turn W1S2 of the second secondary winding 114b, which is electrically connected to pin P4L10, which, in turn, is electrically connected via pin P4L1, capacitors, and pin P3L1 to the first winding W1S1 of the first secondary winding 114a that is located on the first layer L1S1 shown in FIG. 8.

Figure 14:
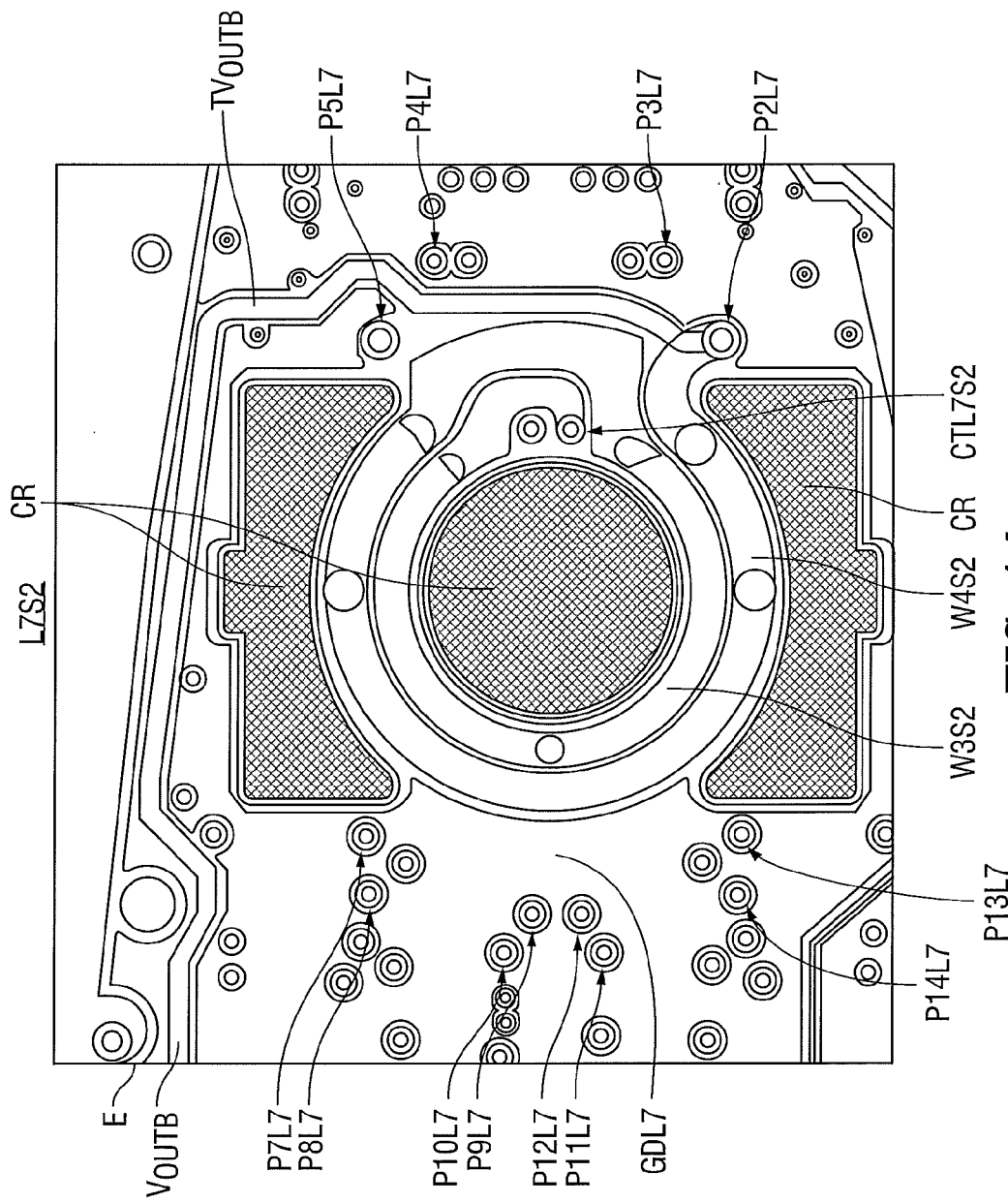
FIG. 14 is a top view of a seventh layer of the planar transformer of FIG. 2.

The tenth layer L10S2 further includes the second turn W2S2 of the second secondary winding 114b, which is electrically connected to the third turn W3S2 of the second secondary winding 114b that is located on the seventh layer L7S2 shown in FIG. 14. The second turn W2S2 is electrically connected to via or contact CTL10S2 located on the tenth layer L10S2, which is electrically connected to via or contact CTL7S2 located on the seventh layer L7S2.

The seventh layer L7S2, shown in FIG. 14, includes the third turn W3S2 of the second secondary winding 114b. The third turn W3S2 is electrically connected via connector CTL7S2 to the second turn W2S2 of the second secondary winding 114b located on the tenth layer L10S2 shown in FIG. 17. The seventh layer L7S2 further includes the fourth turn W4S2 of the second secondary winding 114b, which is electrically connected to pin P2L7 and electrically connects to the load. Pin P2L7 is electrically connected to the trace $TV_{OUTB}$. The trace $TV_{OUTB}$ traverses layer L7S2 to edge E of layer L7S2 where trace $TV_{OUTB}$ exits layer L7S2.

Thus, the electrical pathway through the secondary windings 114a and 114b from $V_{OUTA}$ to $V_{OUTB}$ is as follows: (starting in FIG. 13) trace $TV_{OUTA}$, pin P5L6, (turning to FIG. 11) pin P5L4, fourth turn of the first secondary winding W4S1, third turn of the first secondary winding W3S1, electrical via CTL4S1, (turning to FIG. 8) electrical via CTL1S1, second turn of the first secondary winding W2S1, first turn of the first secondary winding W1S1, pin P3L1, a first capacitor (not shown) that is electrically connected between contacts 804 and 805, conductive trace 802 that is electrically connected between the contacts 804 and 806, a second capacitor (not shown) that is electrically connected between contacts 806 and 807, pin P4L1, (turning to FIG. 17) pin P4L10, first turn of the second secondary winding W1S2, second turn of the second secondary winding W2S2, and electrical via CTL10S2, (turning to FIG. 14) electrical via CTL7S2, third turn of the second secondary winding W3S2, fourth turn of the second secondary winding W4S2, pin P2L7, and trace $TV_{OUTA}$.

The layers L1S1, L4S1, L7S2, and L10S2 each have an associated grounded portion, GDL1, GDL4, GDL7, and GDL10. Each grounded portion GDL1, GDL4, GDL7, and GDL10 is electrically coupled to ground, such as earth ground or circuit board ground. As shown, the grounded portion may be electrically isolated from other parts of the trace on a particular layer.

As shown in FIG. 8, the grounded portion GDL1 of layer 1 covers and extends beyond the second leg of the gap $GP_bL2$ of layer 2, which is adjacent to layer 1. In embodiments, the geometry of the grounded portion may be designed to cover and extend a sufficient distance beyond an adjacent gap to achieve a desired current-spreading effect.

Figure 9:
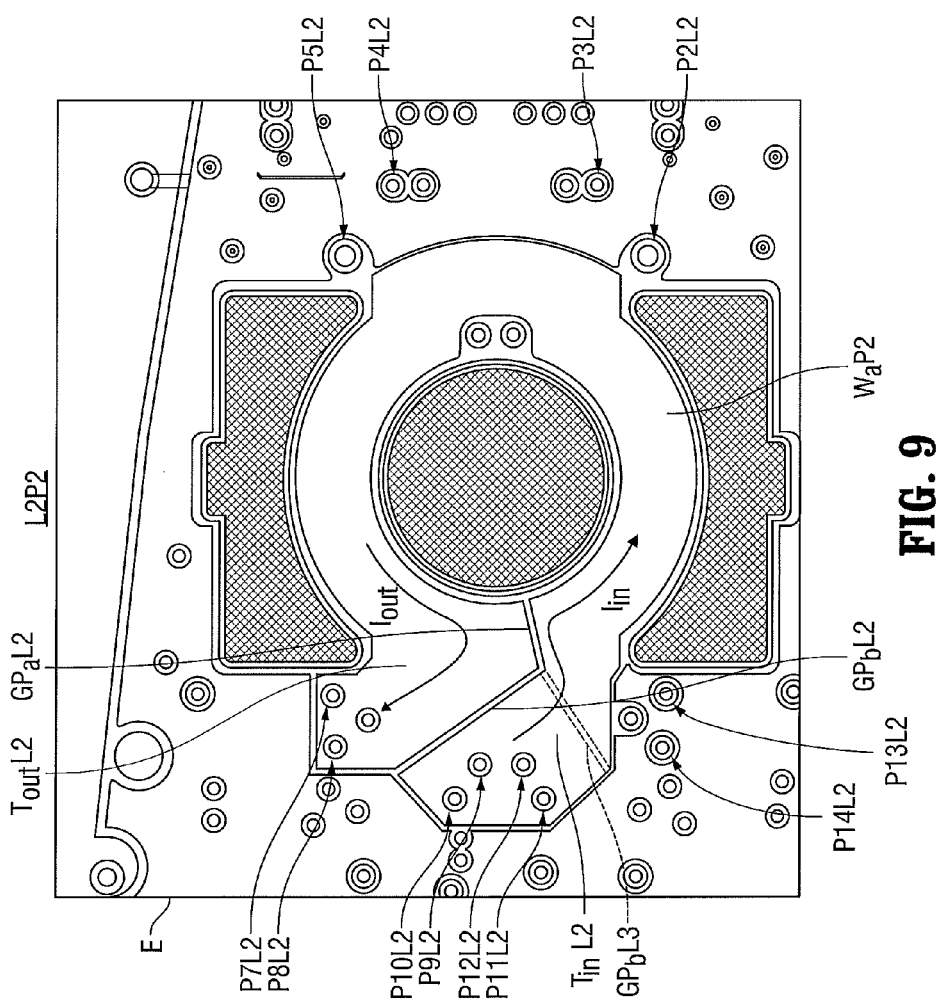
FIG. 9 is a top view of a second layer of the planar transformer of FIG. 2 illustrating another gap between traces disposed on a third layer of the planar transformer of FIG. 2.
Figure 10:
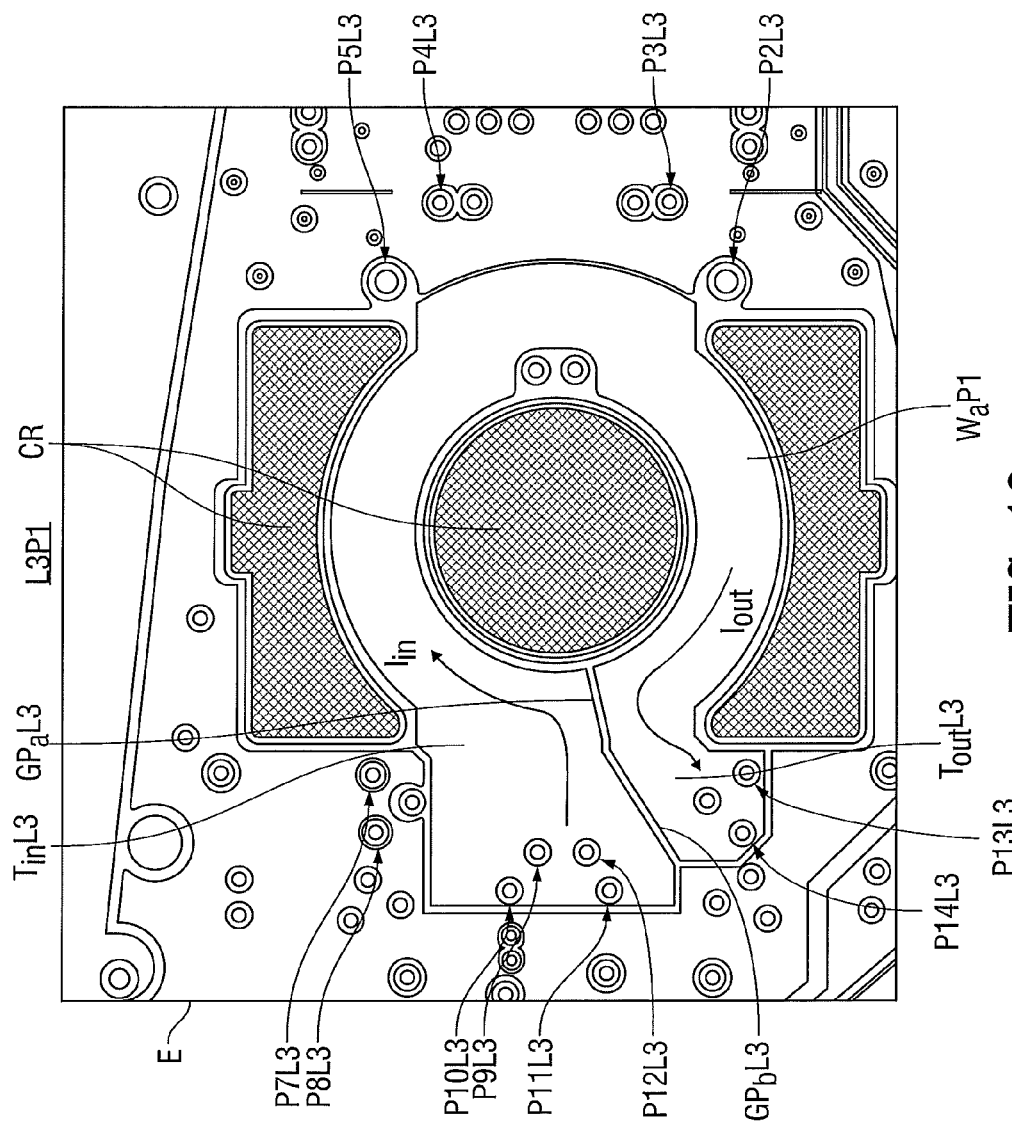
FIG. 10 is a top view of a third layer of the planar transformer of FIG. 2.
Figure 12:
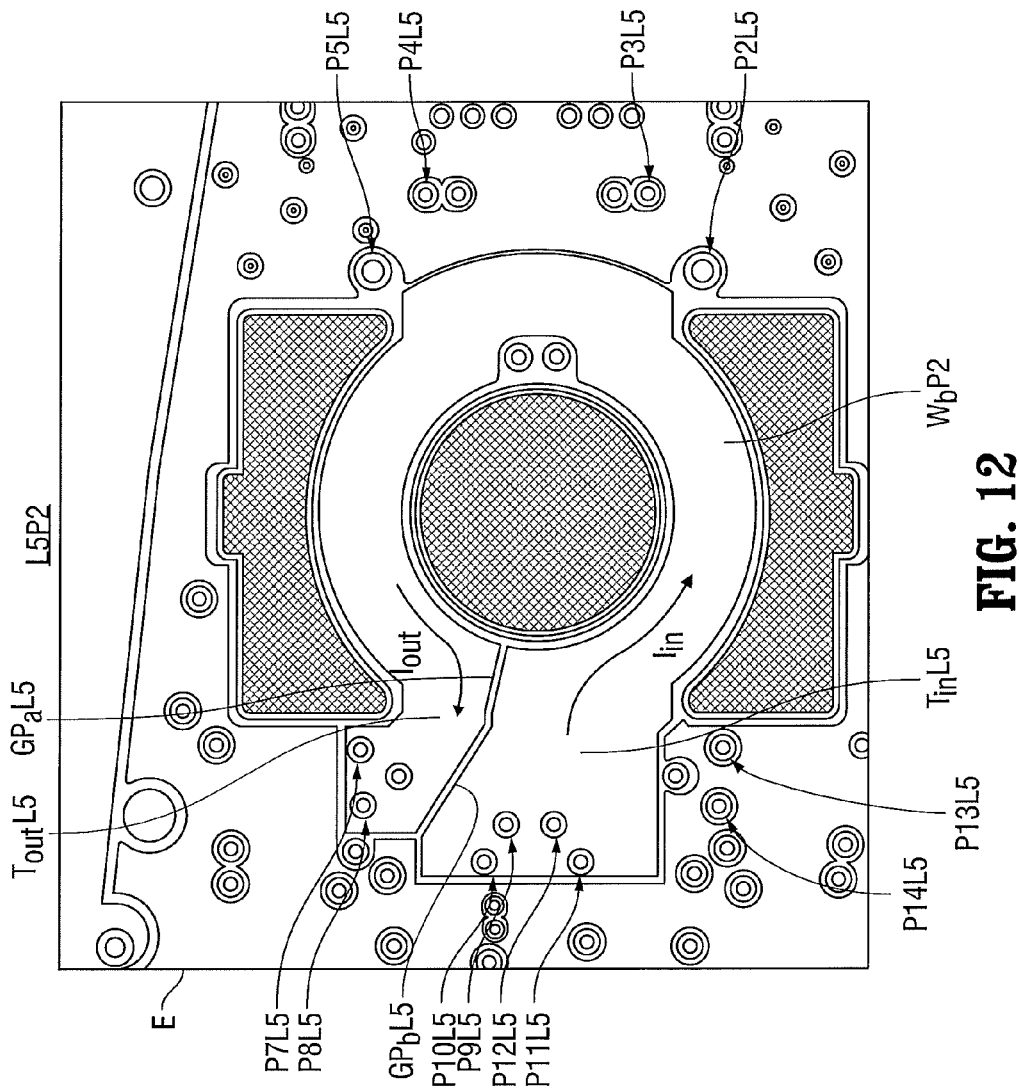
FIG. 12 is a top view of a fifth layer of the planar transformer of FIG. 2.
Figure 13:
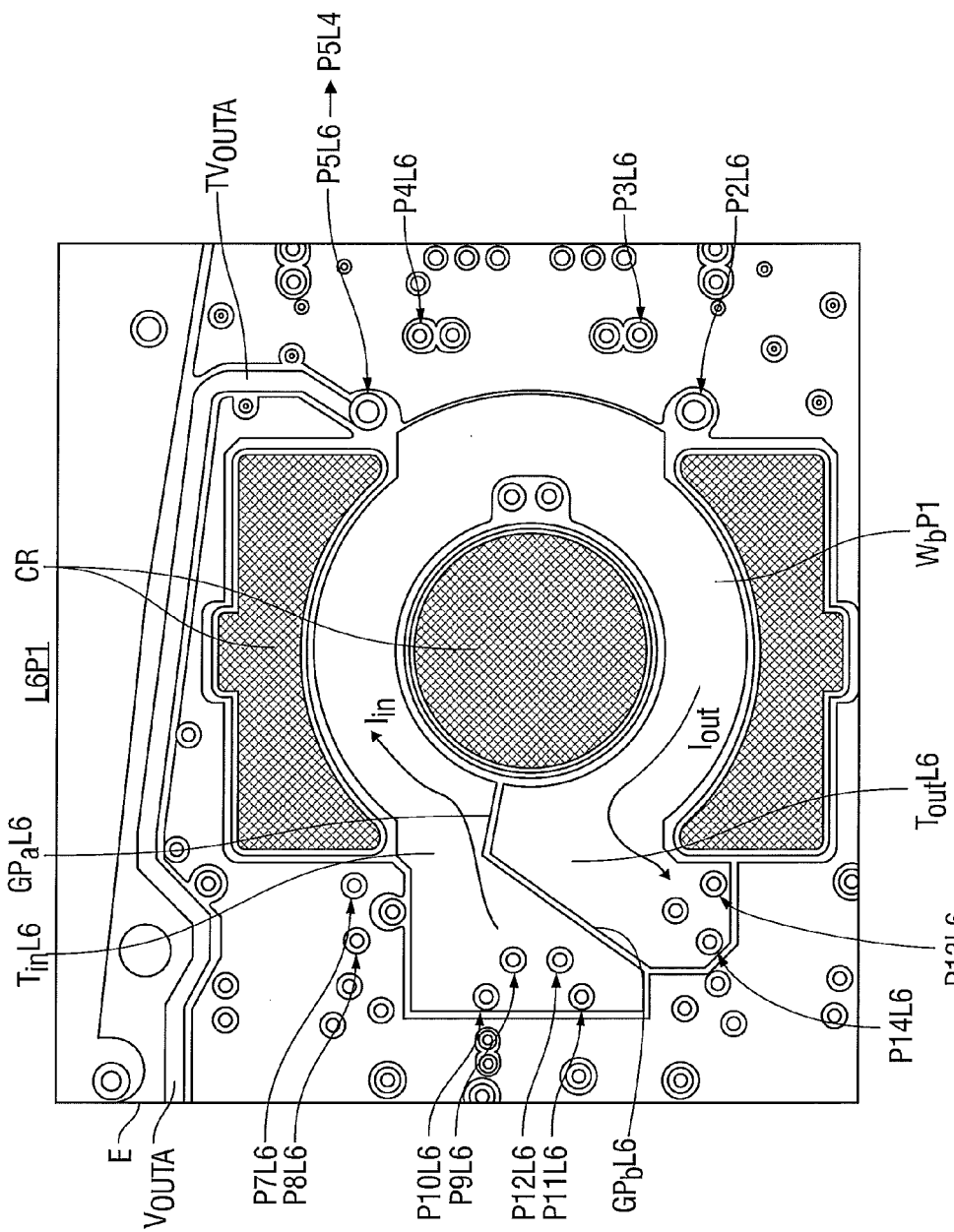
FIG. 13 is a top view of a sixth layer of the planar transformer of FIG. 2.
Figure 15:
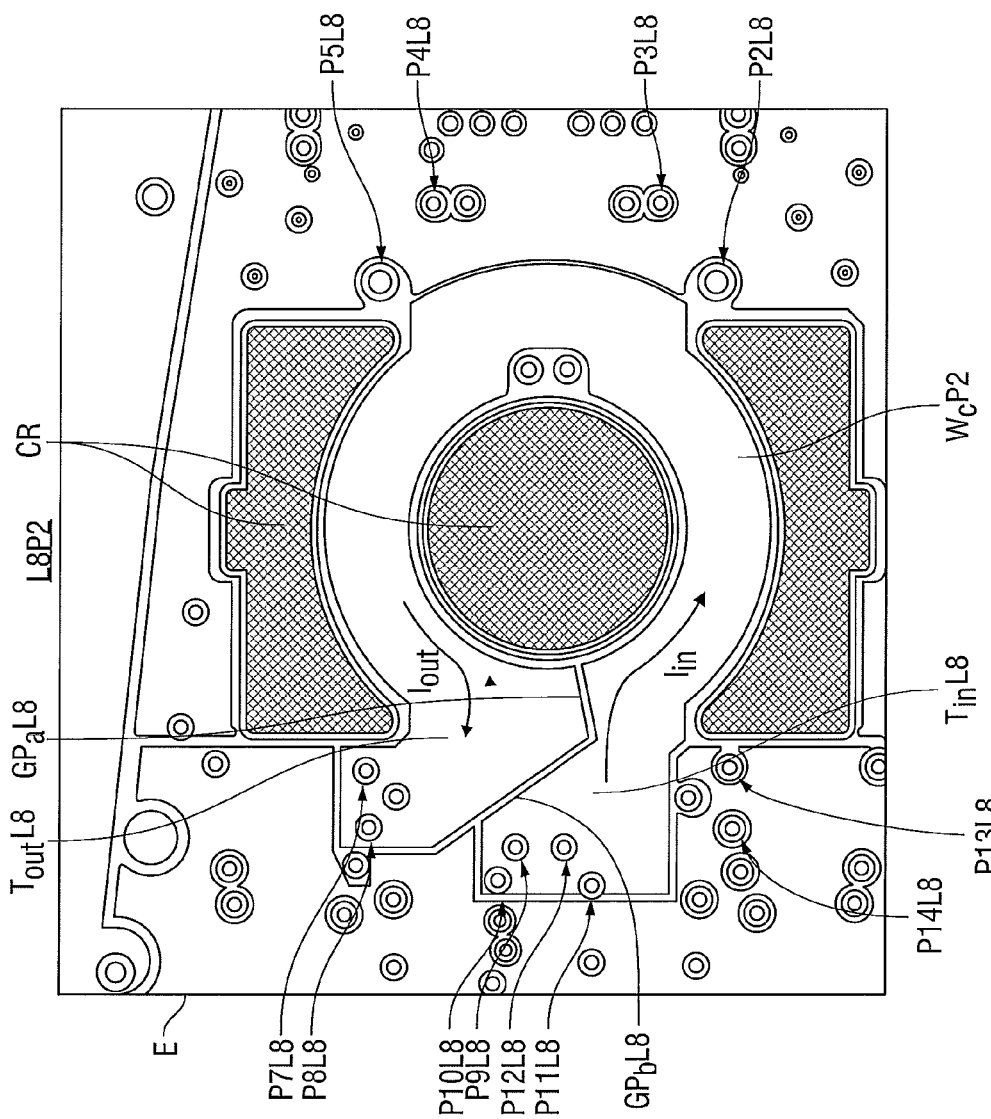
FIG. 15 is a top view of an eighth layer of the planar transformer of FIG. 2.
Figure 16:
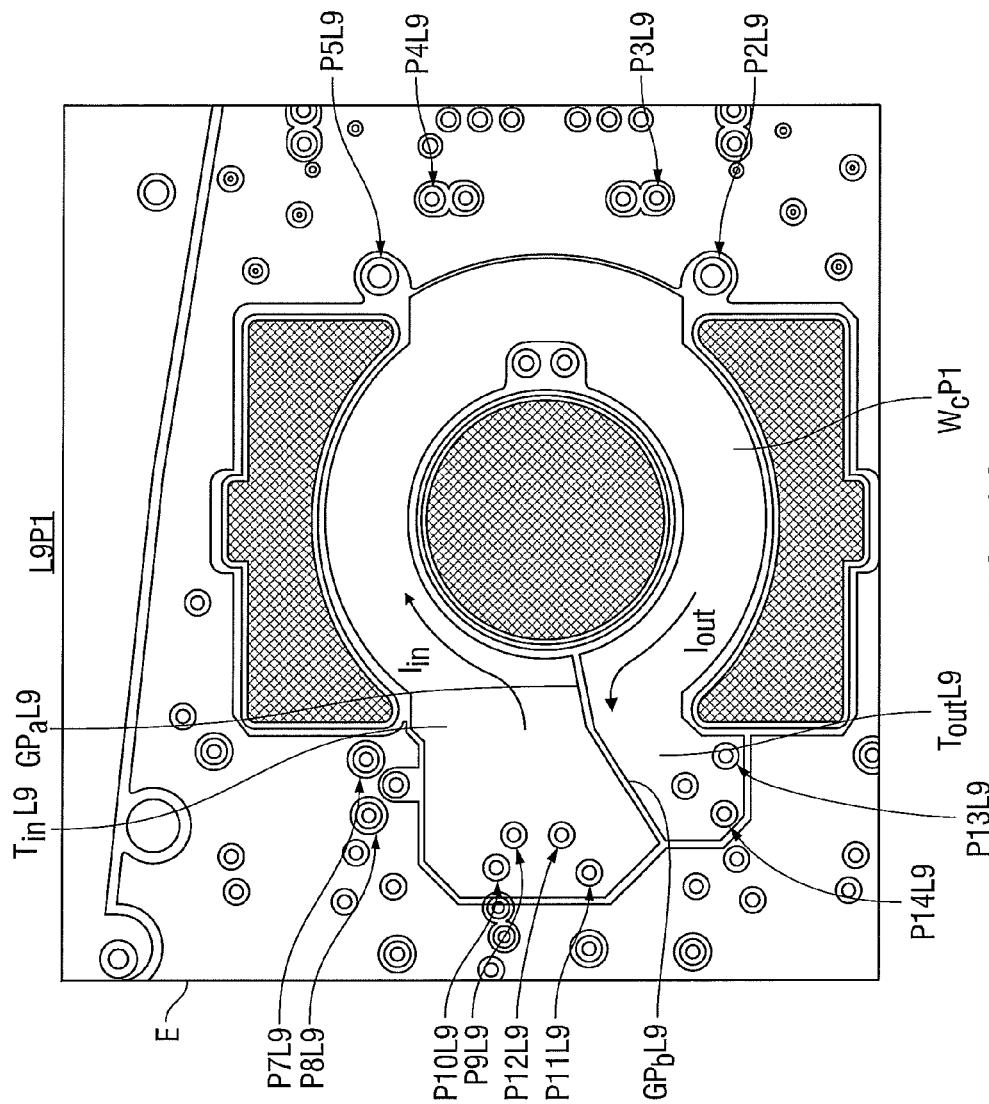
FIG. 16 is a top view of a ninth layer of the planar transformer of FIG. 2.

As shown in FIGS. 10, 13, and 16, the first primary winding 112a includes three windings $W_aP1$, $W_bP1$, and $W_cP1$, which are formed on the third, sixth, and ninth layers L3P1, L6P1, and L9P1, respectively, and which are electrically connected in parallel to form a single turn. Similarly, as shown in FIGS. 9, 12, and 15, the second primary winding 112b includes three windings $W_aP2$, $W_bP2$, and $W_cP2$, which are formed on the second, fifth, and eighth layers L2P2, L5P2, and L8P2, respectively, and which are electrically connected in parallel to form a single turn. In this manner, the current in the first and second primary windings 112a and 112b are shared equally among three windings. Thus, the current density in each winding is one third the current density of a single winding, and, as a result, the losses are one third as large.

With reference to the second layer L2P2 shown in FIG. 9, during a first operational phase (e.g., when the switch 106 is open and the switch 108 is closed as shown in FIG. 1) current is input at pins P9L2, P10L2, P11L2, and P12L2, and flows in the direction shown by the arrows $I_{in}$ and $I_{out}$ (counterclockwise) around the winding $W_aP2$. The current enters the winding $W_aP2$ at first termination portion $T_{in}L2$ and exits the winding $W_aP2$ at second termination portion $T_{out}L2$. During a second operational phase (e.g., when the switch 108 is open and the switch 106 is closed as shown in FIG. 1), the current flows around the winding $W_aP2$ in an opposite direction (clockwise).

The first termination portion $T_{in}L2$ and the second termination portion $T_{out}L2$ are separated by a gap $GP_aL2$. The current entering the winding $W_aP2$ at the first termination portion $T_{in}L2$ and exiting at the second termination portion $T_{out}L2$ flows in opposite directions on either side of the gap $GP_aL2$. The proximity effect causes these currents to crowd together and flow only in a narrow portion of the winding $W_aP2$ when the gaps associated with stacked layers are aligned. In such a configuration, the narrow portion may be approximately one skin-depth, which may be only a few thousandths of an inch for switching power supplies having frequencies over 100 kHz. As described above, to reduce termination losses, which is the power loss caused by this proximity effect, the first and second termination portions of layer L3P1 are configured so that gap $GP_bL3$ (shown in FIG. 9 using hidden lines), is laterally offset from or is not aligned with gap $GP_bL2$.

With respect to the fifth layer L5P2 shown in FIG. 12, during the first operation phase, current $I_{in}$ enters winding $W_bP2$ at pins P9L5, P10L5, P11L5, and P12L5 provided at first termination portion $T_{in}L5$ and current $I_{out}$ (which, for example, corresponds to $I_B$ shown in FIG. 1) exits at pins P7L5 and P8L5 provided at second termination portion $T_{out}L5$. Thus, current flows in a counter-clockwise direction. When the layers L1-L10 are assembled, gap $GP_aL5$, which separates the first termination portion $T_{in}L5$ from the second termination portion $T_{out}L5$, is laterally offset relative to gap $GP_aL2$ shown in FIG. 9.

In addition to the second and fifth layers L2P2 and L5P2 described above, layers L3P1, L6P1, L8P2, and L9P1 include gaps as well. With respect to the third layer L3P1 shown in FIG. 10, during the first operational phase, current $L_{in}$ enters winding $W_aP1$ at pins P9L3, P10L3, P11L3, and P12L3 provided at first termination portion $T_{in}L3$, and exits as current $I_{out}$ (which, for example, corresponds to $I_A$ shown in FIG. 1) at pins P13L3 and P14L3 provided at second termination portion $T_{out}L3$. The gap $GP_aL3$ between the first termination portion $T_{in}L3$ and the second termination portion $T_{out}L3$ is aligned with the gap $GP_aL2$ shown in FIG. 9 but is laterally offset from the gap $GP_aL5$ shown in FIG. 12 when the layers L1-L10 are assembled.

With respect to the sixth layer L6P1 shown in FIG. 13, during the first operational phase, current $I_{in}$ enters the winding $W_bP1$ at pins P9-P12 provided at first termination portion $T_{in}L6$, and exits the winding $W_bP1$ as current $I_{out}$ (which, for example, corresponds to $I_A$ shown in FIG. 1) at pins P13L6 and P14L6 provided at second termination portion $T_{out}L6$. The gap $GP_aL6$ between the first termination portion $T_{in}L6$ and the second termination portion $T_{out}L6$ is aligned with the gap $GP_aL3$ shown in FIG. 10, but is laterally offset from the gaps $GP_aL2$ and $GP_aL3$ shown in FIGS. 9 and 10, respectively, when the layers L1-L10 are assembled.

With respect to the ninth layer L9P1 shown in FIG. 16, during the first operational phase, current $I_{in}$ enters the winding $W_cP1$ at pins P9L9, P10L9, P11L9, and P12L9 provided at the first termination portion $T_{in}L9$, and exits as current $I_{out}$ (which, for example, corresponds to $I_A$ shown in FIG. 1) at pins P13L9 and P14L9 provided at the second termination portion $T_{out}L9$. When the layers L1-L10 are assembled, the gap $GP_aL9$ disposed between the first termination portion $T_{in}L9$ and the second termination portion $T_{out}L9$ is aligned with the gaps $GP_aL2$ and $GP_aL3$ shown in FIGS. 9 and 10, but is laterally offset from the gaps $GP_aL5$ and $GP_aL6$ shown in FIGS. 12 and 13, respectively.

With respect to the eighth layer L8P2 shown in FIG. 15, during the second operational phase, current $I_{in}$ enters the winding $W_cP2$ at pins P9L8, P10L8, P11L8, and P12L8 provided at first termination portion $T_{in}L8$, and exits the winding $W_cP2$ as current $I_{out}$ (which, for example, corresponds to $I_B$ shown in FIG. 1) at pins P7L8 and P8L8 provided at second termination portion $T_{out}L8$. The gap $GP_aL8$, which is disposed between the first termination portion $T_{in}L8$ and the second termination portion $T_{out}L8$, is aligned with the gaps $GP_aL2$, $GP_aL3$, and $GP_aL9$ shown in FIGS. 9, 10, and 16, respectively, but laterally offset from the gaps $GP_aL5$ and $GP_aL6$ shown in FIGS. 12 and 13, respectively, when the layers L1-L10 are assembled.

As described above, the first and second termination portions of the layers having primary windings 112, e.g., layers L2, L3, L5, L6, L8, and L9, are first termination portions and second termination portions, respectively, through which current enters and exits the windings. These first and second termination portions are further configured so that they sufficiently surround and electrically connect to the appropriate pins through which current enters and exits the corresponding winding. For example, in the second layer L2, the first termination portion $T_{in}L2$ is configured to surround and electrically connect to pins P9L2, P10L2, P11L2, and P12L2, and the second termination portion $T_{out}L2$ is configured to surround and electrically connect to pins P7L2 and P8L2. The resulting shape of the first and second termination portions forms a second leg of the gap $GP_bLN$ (where N is selected from 2, 3, 5, 6, 8, and 9) that extends at an angle from the first leg of the gap $GP_aLN$. For each of the above-mentioned layers, the length of the first and second termination portions, as well as the total length of the corresponding gaps $GP_aLN$ and $GP_bLN$, is minimized to further reduce termination losses.

Accordingly, the embodiment of the planar transformer shown in FIGS. 8-17, reduces termination losses in several ways. First, a first leg of a first gap (e.g., $GP_aL6$ of FIG. 13) on a first layer is laterally offset from a first leg of a second gap (e.g., $GP_aL8$ of FIG. 15) on a second layer. Similarly, a second leg of the first gap (e.g., $GP_bL6$ of FIG. 13) on the first layer is laterally offset from a second leg of the second gap (e.g., $GP_bL8$ of FIG. 15) on the second layer. In some embodiments, the gaps may include one or more legs that are laterally offset from each other on different layers. In other embodiments, some groups of gaps on some layers may be laterally offset from other groups of gaps on other layers. In yet other embodiments, only a portion of the gaps on the different layers are laterally offset from each other.

Second, for each layer L1-L10, the total length of the legs of the gaps $GP_aLN$ and $GP_bLN$ is minimized.

Third, termination losses are reduced by positioning the grounded portions GDL1, GDL4, GDL7, and GDL10 of layers L1S1, L4S1, L7S2, and L10S2, respectively adjacent to a portion of the gaps of the other adjacent layers. During operation of the planar transformer, an eddy current is developed in the grounded portions GDL1, GDL4, GDL7, and GDL10 in some layers, which causes current to spread and flow through a larger portion of the first and second termination portions of the other layers.

FIG. 8 shows an example of eddy current ECL1 developed in the grounded portion GDL1 of the first layer L1S1. The eddy current flows in a direction opposite to the direction of the current that flows in the first and second termination portions $T_{in}L2$ and $T_{out}L2$ of the second layer L2P2 near the gap $GP_bL2$. This causes the current in the first and second termination portions $T_{in}L2$ and $T_{out}L2$ to spread, which improves conduction of current in the first and second termination portions $T_{in}L2$ and $T_{out}L2$ and reduces termination losses.

Figure 18A:
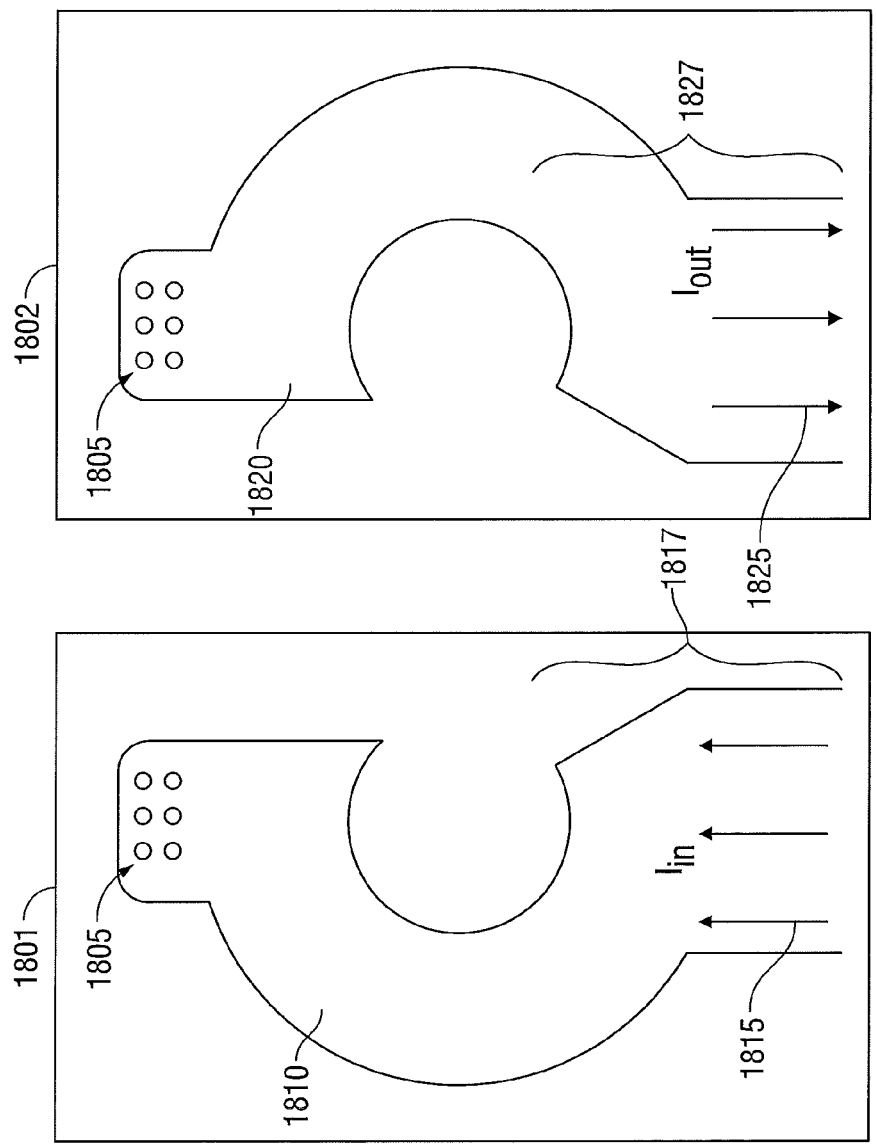
FIG. 18A is an exploded top view of a winding of a planar transformer in accordance with other embodiments of the present disclosure.
Figure 18B:
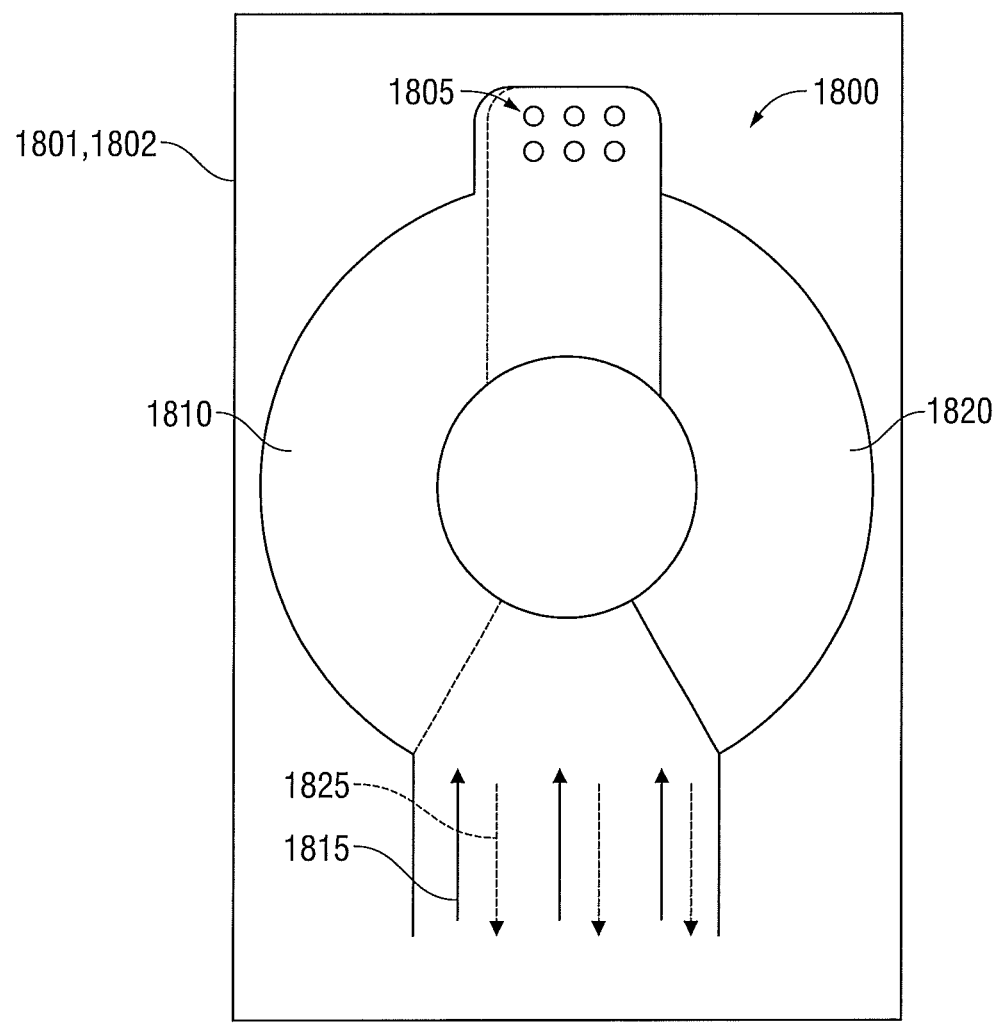
FIG. 18B is a top view of the winding of FIG. 18A in an assembled state.

FIGS. 18A and 18B illustrate a winding of a planar transformer that is formed on two PCB layers to mitigate the proximity effect. As shown in FIG. 18A, the winding includes a first electrically conductive trace 1810 disposed on a first PCB layer 1801 and a second electrically conductive trace 1820 disposed on a second PCB layer 1802. The first electrically conductive trace 1810 forms a first portion of a turn of the winding and the second electrically conductive trace 1820 forms a second remaining portion of the turn of the winding. The first electrically conductive trace 1810 includes a first termination portion 1817 through which current $I_{in}$ may enter the winding and the second electrically conductive trace 1820 includes a second termination portion 1827 through current $I_{out}$ may exit the winding.

As shown in FIG. 18B, the first and second electrically conductive traces 1810 and 1820 are formed so that the first termination portion 1817 overlaps with the second termination portion 1827 when the first and second PCB layers are stacked together in a first direction, i.e., in a direction perpendicular to the surface of the page. In other words, the first and second electrically conductive traces 1810 and 1820 are formed so that the first termination portion 1817 is aligned with the second termination portion 1827 in a second direction perpendicular to the first direction, i.e., in a direction parallel to the surface of the page, when the first and second PCB layers are stacked together in the first direction.

Thus, in this configuration, the first electrically conductive trace 1810 on the first layer 1801 forms a first portion of the winding and the second electrically conductive trace 1820 on the second layer 1802 forms the second remaining portion of the winding. In embodiments, the first electrically conductive trace 1810 may form more or less than half of the turn of the winding, e.g., three quarters of the turn of the winding, and the second electrically conductive trace may form the remaining portion of the turn of the winding, e.g., one quarter of the turn of the winding.

The first and second electrically conductive traces 1810 and 1820 are electrically connected to each other by one or more electrical vias 1805 to form one turn of the winding 1800. This turn of the winding 1800 may be used for each of the turns of the first and second primary windings 112a and 112b described above. In embodiments, multiple windings 1800 may be formed on multiple circuit layers, e.g., three turns on six circuit layers, and electrically connected in parallel to the form the first and second primary windings 112a and 112b described above.

As shown in FIG. 18B, input current 1815 may flow into a first end of the first electrically conductive trace 1810 of the first PCB layer 1801 and then may flow out of a second end of the first electrically conductive trace 1810 through the electrical vias 1805 to a second end of the second electrically conductive trace 1820 of the second PCB layer 1802. The current then flows through the second electrically conductive trace 1820 and exits as second end of the second electrically conductive trace 1820 as output current 1825. As shown in FIG. 18B, the input and output currents 1815 and 1825 "mirror" each other and spread out over the entire width of the first and second termination portions 1817 and 1827 of the first and second electrically conductive traces 1810 and 1820, respectively. As a result, termination losses are reduced.

In embodiments, the planar transformer of the present disclosure may include a first set of primary windings that are formed according to the winding 1800 of FIGS. 18A and 18B and a second set of primary windings formed according to the primary windings $W_aP1$, $W_aP2$, $W_bP1$, $W_bP2$ $W_cP1$, and $W_cP2$ of FIGS. 9, 10, 12, 13, 15, and 16, respectively. For example, the primary winding may include a third electrically conductive trace disposed on a third PCB layer and a fourth electrically conductive trace disposed on a fourth PCB layer. The third electrically conductive trace may form at least one winding having a first termination portion and a second termination portion that are separated by a first gap. The fourth electrically conductive trace may form at least one winding having a first termination portion and a second termination portion that are separated by a second gap that is offset relative to the first gap in a second direction.

In embodiments, the planar transformer of the present disclosure may further include a fifth PCB layer having an electrically conductive trace that forms a grounded portion coupled to ground. The fifth PCB layer may be formed so that the grounded portion is aligned with at least one of the first and second gaps in the first direction.

Figure 19:
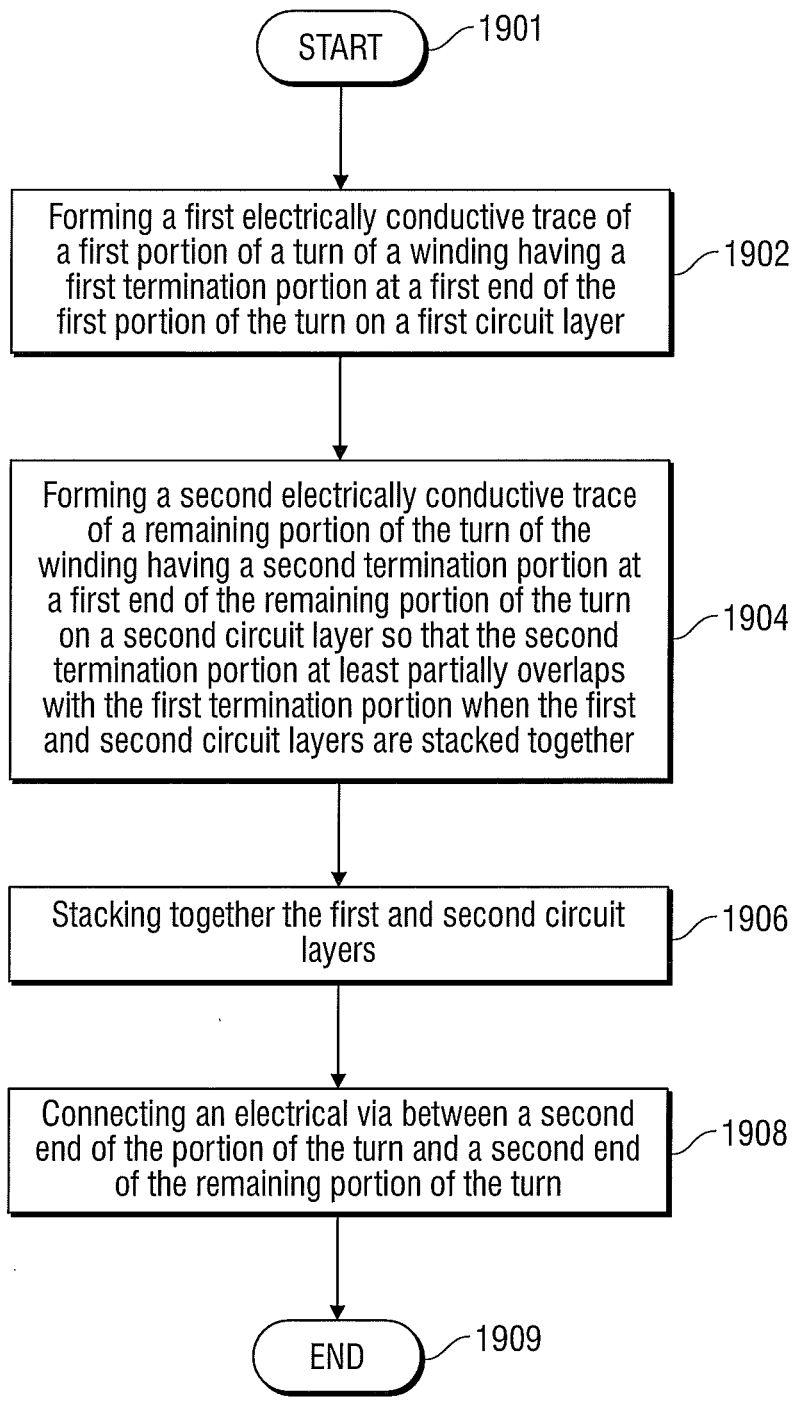
FIG. 19 is a flow diagram illustrating a method of manufacturing a planar transformer according to embodiments of the present disclosure.

FIG. 19 is a flow diagram illustrating a method of manufacturing a planar transformer having a first portion of a turn of a winding disposed on a first PCB layer and a second portion of the turn of the winding disposed on a second PCB layer. After the method starts in step 1901, a first electrically conductive trace of a first portion of a turn of a winding (e.g., the electrically conductive trace 1810 of FIG. 18A) is formed on a first PCB layer (e.g., the circuit layer 1801 of FIG. 18A) in step 1902. The first portion of the turn includes a first termination portion (e.g., the termination portion 1817 of FIG. 18A) at a first end of the first portion of the turn.

In step 1904, a second electrically conductive trace (e.g., the electrically conductive trace 1820 of FIG. 18A) of a second remaining portion of the turn of the winding is formed on a second PCB layer (e.g., the circuit layer 1802 of FIG. 18A). The second remaining portion of the turn includes a second termination portion (e.g., the termination portion 1827 of FIG. 18A) at a first end of the second remaining portion of the turn. The second termination portion is formed so that it at least partially overlaps with the first termination portion when the first and second circuit layers are stacked together. Alternatively, the first and second termination portions may both be formed so that the first termination portion at least partially overlaps with the first termination portion when the first and second circuit layers are stacked together.

In step 1906, the first and second layers are stacked together. Then, before the method ends in step 1909, an electrical via or multiple electrical vias (e.g., the electrical vias 1805 of FIG. 18A) are connected between a second end of the first portion of the turn and a second end of the remaining portion of the turn in step 1908. The result of the method of manufacturing of FIG. 19 may be the stack of circuit layers 1801 and 1802 shown in FIG. 18B where the first and second termination portions substantially overlap each other.

As used herein, the term "form" refers to any known manufacturing process for creating electrically conductive traces on the surface of a substrate. The manufacturing process may involve bonding a layer of electrically conductive material (e.g., copper) over the entire substrate, then removing unwanted electrically conductive material after applying a temporary mask (e.g., by etching), thereby leaving the desired electrically conductive material. Alternatively, the manufacturing process may involve adding electrically conductive traces to the substrate by performing an electroplating process.

Figure 20:
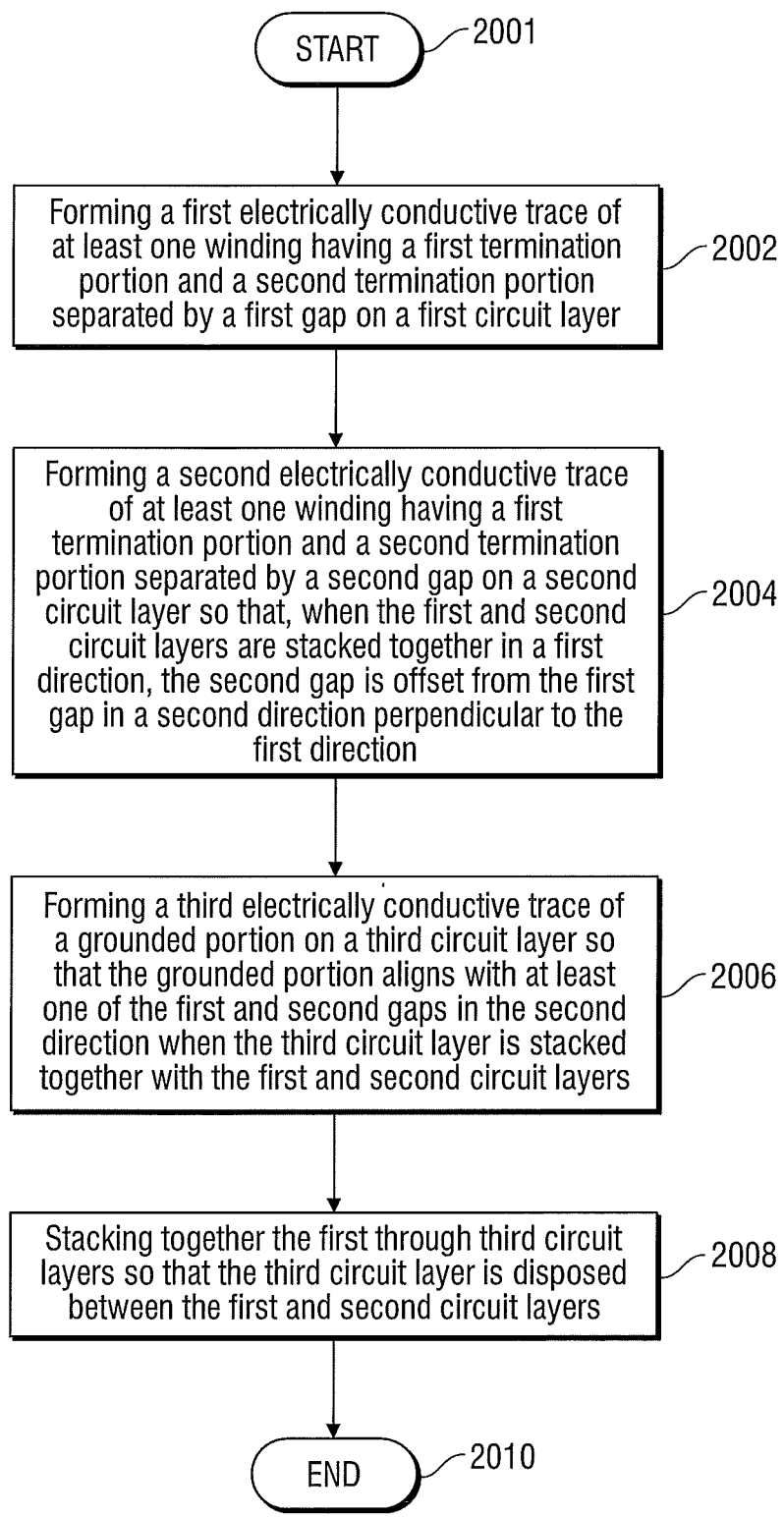
FIG. 20 is a flow diagram illustrating a method of manufacturing a planar transformer according to embodiments of the present disclosure.

FIG. 20 is a flow diagram illustrating a method of manufacturing a planar transformer according to embodiments of the present disclosure. This method may be performed in the alternative to or in addition to the method of manufacturing of FIG. 19. For example, the method of manufacturing of FIG. 19 may be employed to manufacture the primary windings of the planar transformer while the method of manufacturing of FIG. 20 may be employed to manufacture the secondary windings of the planar transformer. Alternatively, the method of manufacturing of FIG. 19 may be employed to manufacture a first set of primary windings of a planar transformer while the method of manufacturing of FIG. 20 may be employed to manufacture a second set of primary windings of the planar transformer.

After the method of manufacturing starts in step 2001, a first electrically conductive trace of at least one winding (e.g., the electrically conductive trace of winding $W_aP2$ of FIG. 9) is formed on a first circuit layer (e.g., the second layer L2P2 of FIG. 9) in step 2002. The first electrically conductive trace includes a first termination portion (e.g., the first termination portion $T_{in}L2$) and a second termination portion (e.g., the second termination portion $T_{out}L2$) separated by a first gap (e.g., the second leg of the gap $GP_bL2$).

In step 2004, a second electrically conductive trace of at least one winding (e.g., the electrically conductive trace of winding $W_aP1$ of FIG. 10) is formed on a second circuit layer (e.g., the second layer L3P1 of FIG. 10). The second electrically conductive trace is formed to include a first termination portion (e.g., the first termination portion $T_{in}L3$) and a second termination portion (e.g., the second termination portion $T_{out}L3$) separated by a second gap (e.g., the second leg of the gap $GP_bL3$) so that, when the first and second circuit layers are stacked together in a first direction, the second gap is offset from the first gap in a second direction perpendicular to the first direction. In other words, if the first and second circuit layers are stacked in a vertical direction, the first and second gaps are laterally offset from each other.

In step 2006, a third electrically conductive trace of a grounded portion is formed on a third circuit layer so that the grounded portion aligns with the at least one of the first and second gaps in the second direction when the third circuit layer is stacked together with the first and second circuit layers. The third electrically conductive trace may span an area that is larger than the area spanned by the at least one of the first and second gaps. In step 2008, the first through third circuit layers are stacked together so that the third circuit layer is disposed between the first and second circuit layers. Then, the method of manufacturing a planar transformer ends in step 2010.

In embodiments, the methods of manufacturing may further include inserting a core through at least one aperture formed in the circuit layers. The method may further include assembling the planar transformer with at least one other component for forming a generator. The method may further include assembling the planar transformer with at least one other component for forming a generator of an electrosurgical instrument.

Figure 21:
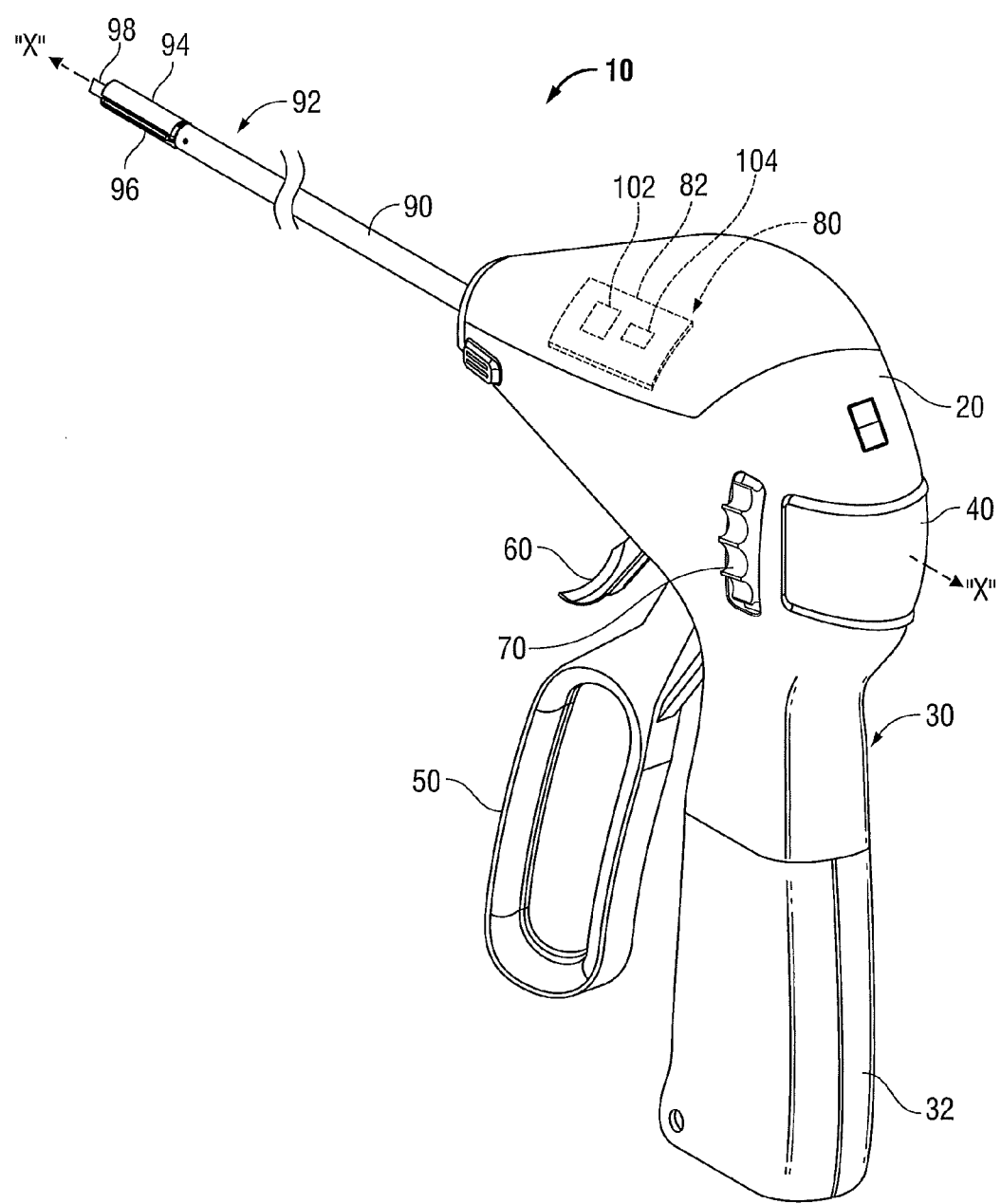
FIG. 21 is a perspective view of an electrosurgical instrument including a generator circuit board having a planar transformer in accordance with embodiments of the present disclosure.

FIG. 21 shows an exemplary electrosurgical instrument 10 that may incorporate the planar transformer according to embodiments of the present disclosure. The instrument 10 includes a housing 20, a handpiece assembly 30, an activation switch 40, a lever 50, a trigger 60, a rotation actuator 70, a generator assembly 80, and a shaft 90. An end effector assembly 92 may be mechanically engaged at the distal end of shaft 90 having a longitudinal axis "X-X". A battery 32 may attach to the handpiece assembly 30 so that the surgeon holds the instrument 10 by grasping the handpiece assembly 30 together with the battery 32.

A delivery device, e.g., end effector assembly 92, may include one or more mechanisms for performing a surgical task, such as applying energy to tissue, stapling, clamping, cauterizing, coagulating, desiccating, and/or cutting. The instrument 10 is a forceps having opposing first and second jaw members 94 and 96. However, other varieties of surgical instruments are envisioned that deliver energy for operating the instrument and/or for applying energy to tissue. Both jaw members 94 and 96 may be moveable with respect to the other, such as for grasping and manipulating tissue. Further, one or both of the jaw members 94, 96 may include energy application surfaces that may be disposed in opposed relation relative to one another. RF energy may be supplied to one or both application surfaces of the jaw members 94, 96 such as to treat or seal tissue grasped therebetween. A knife 98 may be provided that may be advanced between the jaw members 94 and 96, e.g., to sever sealed tissue disposed between the opposing jaw members 94 and 96.

The instrument 10 includes several actuators that are actuated by the surgeon for controlling respective subsystems of instrument 10. The activation switch 40 controls delivery of energy in response to actuation. The lever 50 controls operation of the end effector assembly 92, e.g., for opening and closing the jaw members 94 and 96 relative to one another for clamping and releasing tissue. The trigger 60 controls deployment of the knife 98. The rotation actuator 70, controls rotation of shaft 90 about longitudinal axis X-X, e.g., for rotating the end effector assembly 92 and/or the knife 98.

Both the battery 32 and the generator assembly 80 are operably coupled to housing 20 and may be selectively removable therefrom. The battery 32 is configured to electrically couple to the generator assembly 80 for powering the generator assembly 80 to generate electrosurgical energy, e.g., RF energy. The generator assembly 80, in turn, supplies the desired electrosurgical energy to the energy application surfaces of the jaw members 94, 96 for delivery to tissue.

The generator assembly 80 also includes one or more PCBs 82. The RF inverter circuit 102, which includes the planar transformer 100, and a microcontroller 104 are electrically coupled to the PCBs 82. The microcontroller 104 generates control signals (e.g., the signals PWM1 and PWM2 of FIG. 1), which are used to control the RF inverter circuit 102 to generate electrosurgical energy. The microcontroller 104 may further control, for example, the functions of the instrument 10, signal processing, and analog-to-digital conversion.

From the foregoing and with reference to the various figure drawings, those skilled in the art will appreciate that certain modifications can be made to the present disclosure without departing from the scope of the same. For example, the windings of the planar transformer may be provided in a variety of configurations, including a variety of shapes; a variety of turns ratios; and providing windings that are formed by electrically connecting conductive traces in series or in parallel on different circuit layers.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a planar transformer, the method comprising:
    forming a first primary electrically conductive trace of at least one winding on a first circuit layer, the first primary electrically conductive trace having a first termination portion and a second termination portion defining a first gap therebetween;
    forming a second primary electrically conductive trace of at least one winding on a second circuit layer, the second primary electrically conductive trace having a first termination portion and a second termination portion defining a second gap therebetween so that, when the first and second circuit layers are stacked together in a first direction, the second gap is offset from the first gap in a second direction perpendicular to the first direction;
    forming a first secondary electrically conductive trace of at least one winding on a third circuit layer; and
    forming an electrically conductive trace into a grounded portion on the third circuit layer so that the grounded portion aligns with at least one of the first and second gaps in the second direction when the third circuit layer is stacked together with the first and second circuit layers.

2. The method of manufacturing according to claim 1, further comprising stacking together the first through third circuit layers so that the third circuit layer is disposed between the first and second circuit layers.

3. The method of manufacturing according to claim 1, further comprising stacking together the first and second circuit layers.

4. The method of manufacturing according to claim 3, further comprising inserting a core through at least one aperture formed in the first and second circuit layers.

5. The method of manufacturing according to claim 1, further comprising assembling the planar transformer with at least one other component for assembling a generator.

6. The method of manufacturing according to claim 1, further comprising assembling the planar transformer with at least one other component for assembling a generator of an electrosurgical instrument.

* * * * *